United States Patent
Garabedian et al.

(10) Patent No.: US 8,185,208 B2
(45) Date of Patent: *May 22, 2012

(54) MODULAR STIMULATION LEAD NETWORK

(75) Inventors: Robert J. Garabedian, Mountain View, CA (US); Michael P. Wallace, Fremont, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 12/549,223

(22) Filed: Aug. 27, 2009

(65) Prior Publication Data

US 2009/0319012 A1    Dec. 24, 2009

Related U.S. Application Data

(63) Continuation of application No. 10/799,271, filed on Mar. 12, 2004, now Pat. No. 7,590,454.

(51) Int. Cl.
*A61N 1/34* (2006.01)
(52) U.S. Cl. .......................... 607/46; 607/117
(58) Field of Classification Search .................. 607/46, 607/115–118
See application file for complete search history.

(56) References Cited

U.S. PATENT DOCUMENTS

| | | | |
|---|---|---|---|
| 538,514 A | 4/1895 | Haeseler | |
| 661,047 A | 11/1900 | Graves | |
| 4,141,365 A | 2/1979 | Fischell et al. | |
| 4,285,347 A | 8/1981 | Hess | |
| 4,519,403 A | 5/1985 | Dickhudt | |
| 4,608,985 A | 9/1986 | Crish et al. | |
| 4,658,835 A | 4/1987 | Pohndorf | |
| 4,739,768 A | 4/1988 | Engelson | |
| 4,813,934 A | 3/1989 | Engelson et al. | |
| 4,869,255 A | 9/1989 | Putz | |
| 4,884,579 A | 12/1989 | Engelson | |
| 5,005,587 A | 4/1991 | Scott | |
| 5,010,894 A | 4/1991 | Edhag | |
| 5,010,895 A | 4/1991 | Maurer et al. | |

(Continued)

FOREIGN PATENT DOCUMENTS

EP    0861676    9/1998

(Continued)

OTHER PUBLICATIONS

PCT International Search Report for PCT/US2005/010121, Applicant: Boston Scientific Scimed, Inc, Forms PCT/ISA/210 and 220, dated Jul. 4, 2005 (7 pages).

(Continued)

*Primary Examiner* — Brian T Gedeon
(74) *Attorney, Agent, or Firm* — Vista IP Law Group LLP

(57) ABSTRACT

A medical kit and method for treating an ailment, such as chronic pain is provided. The kit comprises first and second medical leads, e.g., stimulation leads. Each lead comprises an elongated body and at least one operative element. The first medical lead comprises a coupling mechanism, such as a slot, and the second medical lead comprises a complementary mechanism, such as a rail, that slidably engages the coupling mechanism of the first medical lead. The method may comprise delivering the first medical lead into a patient's body, e.g., into the epidural space of the patient, and delivering the second medical lead into the patient's body by sliding the complementary coupling mechanism of the second medical lead along the coupling mechanism of the first medical lead.

27 Claims, 15 Drawing Sheets

U.S. PATENT DOCUMENTS

| | | |
|---|---|---|
| 5,107,856 A | 4/1992 | Kristiansen et al. |
| 5,170,802 A | 12/1992 | Mehra |
| 5,224,491 A | 7/1993 | Mehra |
| 5,234,437 A | 8/1993 | Sepetka |
| 5,239,999 A | 8/1993 | Imran |
| 5,250,071 A | 10/1993 | Palermo |
| 5,261,916 A | 11/1993 | Engelson |
| 5,263,488 A | 11/1993 | Van Veen et al. |
| 5,304,195 A | 4/1994 | Twyford, Jr. et al. |
| 5,306,272 A | 4/1994 | Cohen et al. |
| 5,312,415 A | 5/1994 | Palermo |
| 5,342,410 A | 8/1994 | Braverman |
| 5,350,397 A | 9/1994 | Palermo et al. |
| 5,358,514 A | 10/1994 | Schulman et al. |
| 5,365,926 A | 11/1994 | Desai |
| 5,374,285 A | 12/1994 | Vaini et al. |
| 5,385,528 A | 1/1995 | Wilk |
| 5,391,200 A | 2/1995 | KenKnight et al. |
| 5,397,341 A | 3/1995 | Hirschberg et al. |
| 5,411,551 A | 5/1995 | Winston et al. |
| 5,417,719 A | 5/1995 | Hull et al. |
| 5,423,864 A | 6/1995 | Ljungstroem |
| 5,423,877 A | 6/1995 | Mackey |
| 5,443,492 A | 8/1995 | Stokes et al. |
| 5,462,545 A | 10/1995 | Wang et al. |
| 5,464,446 A | 11/1995 | Dreessen et al. |
| 5,501,703 A | 3/1996 | Holsheimer et al. |
| 5,509,411 A | 4/1996 | Littmann et al. |
| 5,531,779 A | 7/1996 | Dahl et al. |
| 5,534,007 A | 7/1996 | St. Germain et al. |
| 5,543,864 A | 8/1996 | Hirschman et al. |
| 5,582,609 A | 12/1996 | Swanson et al. |
| 5,603,731 A | 2/1997 | Whitney |
| 5,611,345 A | 3/1997 | Hibbeln |
| 5,647,870 A | 7/1997 | Kordis et al. |
| 5,683,422 A | 11/1997 | Rise |
| 5,702,438 A | 12/1997 | Avitali |
| 5,707,354 A | 1/1998 | Salmon et al. |
| 5,713,922 A | 2/1998 | King |
| 5,716,377 A | 2/1998 | Rise et al. |
| 5,752,979 A | 5/1998 | Benabid |
| 5,755,750 A | 5/1998 | Petruska et al. |
| 5,782,239 A | 7/1998 | Webster, Jr. et al. |
| 5,782,798 A | 7/1998 | Rise |
| 5,792,187 A | 8/1998 | Adams |
| 5,800,474 A | 9/1998 | Benabid et al. |
| 5,814,062 A | 9/1998 | Sepetka et al. |
| 5,833,709 A | 11/1998 | Rise et al. |
| 5,846,196 A | 12/1998 | Siekmeyer et al. |
| 5,846,238 A | 12/1998 | Jackson et al. |
| 5,860,974 A | 1/1999 | Abele et al. |
| 5,871,483 A | 2/1999 | Jackson et al. |
| 5,891,136 A | 4/1999 | McGee et al. |
| 5,902,236 A | 5/1999 | Iverson |
| 5,902,331 A | 5/1999 | Bonner et al. |
| 5,908,385 A | 6/1999 | Chechelski et al. |
| 5,925,070 A | 7/1999 | King et al. |
| 5,928,278 A | 7/1999 | Kitschmann |
| 5,931,862 A | 8/1999 | Carson |
| 5,938,689 A | 8/1999 | Fischell et al. |
| 5,954,761 A | 9/1999 | Machek et al. |
| 5,967,986 A | 10/1999 | Cimochowski et al. |
| 5,984,909 A | 11/1999 | Lurie et al. |
| 6,002,964 A | 12/1999 | Feler et al. |
| 6,006,124 A | 12/1999 | Fischell et al. |
| 6,006,134 A | 12/1999 | Hill et al. |
| 6,015,387 A | 1/2000 | Schwartz et al. |
| 6,016,449 A | 1/2000 | Fischell et al. |
| 6,018,682 A | 1/2000 | Rise |
| 6,027,456 A | 2/2000 | Feler et al. |
| 6,036,689 A | 3/2000 | Tu et al. |
| 6,053,873 A | 4/2000 | Govari et al. |
| 6,066,163 A | 5/2000 | John |
| 6,074,407 A | 6/2000 | Levine et al. |
| 6,074,507 A | 6/2000 | Sukenik |
| 6,091,980 A | 7/2000 | Squire et al. |
| 6,094,596 A | 7/2000 | Morgan |
| 6,119,044 A | 9/2000 | Kuzma |
| 6,122,548 A | 9/2000 | Starkebaum et al. |
| 6,128,537 A | 10/2000 | Rise |
| 6,128,538 A | 10/2000 | Fischell et al. |
| 6,136,021 A | 10/2000 | Tockman et al. |
| 6,141,576 A | 10/2000 | Littmann et al. |
| 6,152,899 A | 11/2000 | Farley et al. |
| 6,161,029 A | 12/2000 | Spreigl et al. |
| 6,161,047 A | 12/2000 | King et al. |
| 6,170,488 B1 | 1/2001 | Spillman, Jr. et al. |
| 6,179,858 B1 | 1/2001 | Squire et al. |
| 6,192,279 B1 | 2/2001 | Barreras, Sr. et al. |
| 6,192,280 B1 | 2/2001 | Sommer et al. |
| 6,205,361 B1 | 3/2001 | Kuzma et al. |
| 6,216,045 B1 | 4/2001 | Black et al. |
| 6,231,516 B1 | 5/2001 | Keilman et al. |
| 6,249,707 B1 | 6/2001 | Kohnen et al. |
| 6,263,248 B1 | 7/2001 | Farley et al. |
| 6,266,568 B1 | 7/2001 | Mann et al. |
| 6,292,702 B1 | 9/2001 | King et al. |
| 6,319,241 B1 | 11/2001 | King et al. |
| 6,319,251 B1 | 11/2001 | Tu et al. |
| 6,330,477 B1 | 12/2001 | Casavant |
| 6,353,762 B1 | 3/2002 | Baudino et al. |
| 6,360,122 B1 | 3/2002 | Fischell et al. |
| 6,361,528 B1 | 3/2002 | Wilson et al. |
| 6,370,427 B1 | 4/2002 | Alt et al. |
| 6,391,052 B2 | 5/2002 | Buirge et al. |
| 6,391,643 B1 | 5/2002 | Chen et al. |
| 6,393,325 B1 | 5/2002 | Mann et al. |
| 6,397,109 B1 | 5/2002 | Cammilli et al. |
| 6,402,746 B1 | 6/2002 | Whayne et al. |
| 6,408,214 B1 | 6/2002 | Williams et al. |
| 6,415,187 B1 | 7/2002 | Kuzma et al. |
| 6,418,344 B1 | 7/2002 | Rezai et al. |
| 6,430,442 B1 | 8/2002 | Peters et al. |
| 6,438,427 B1 | 8/2002 | Rexhausen et al. |
| 6,442,413 B1 | 8/2002 | Silver |
| 6,442,435 B2 | 8/2002 | King et al. |
| 6,445,953 B1 | 9/2002 | Bulkes et al. |
| 6,463,328 B1 | 10/2002 | John |
| 6,466,822 B1 | 10/2002 | Pless |
| 6,480,743 B1 | 11/2002 | Kirkpatrick et al. |
| 6,484,059 B2 | 11/2002 | Gielen |
| 6,510,347 B2 | 1/2003 | Borkan |
| 6,516,227 B1 | 2/2003 | Meadows et al. |
| 6,519,488 B2 | 2/2003 | KenKnight et al. |
| 6,522,932 B1 | 2/2003 | Kuzma et al. |
| 6,529,774 B1 | 3/2003 | Greene |
| 6,539,263 B1 | 3/2003 | Schiff |
| 6,547,788 B1 | 4/2003 | Maguire et al. |
| 6,547,870 B1 | 4/2003 | Griessmann et al. |
| 6,562,063 B1 | 5/2003 | Euteneuer et al. |
| 6,584,358 B2 | 6/2003 | Carter et al. |
| 6,587,733 B1 | 7/2003 | Cross, Jr. et al. |
| 6,589,230 B2 | 7/2003 | Gia et al. |
| 6,591,138 B1 | 7/2003 | Fischell et al. |
| 6,597,953 B2 | 7/2003 | Boling |
| 6,600,954 B2 | 7/2003 | Cohen et al. |
| 6,600,956 B2 | 7/2003 | Maschino et al. |
| 6,606,521 B2 | 8/2003 | Paspa et al. |
| 6,625,496 B1 | 9/2003 | Ollivier |
| 6,647,296 B2 | 11/2003 | Fischell et al. |
| 6,658,302 B1 | 12/2003 | Kuzma et al. |
| 6,662,055 B1 | 12/2003 | Prutchi |
| 6,665,562 B2 | 12/2003 | Gluckman et al. |
| 6,671,544 B2 | 12/2003 | Baudino |
| 6,675,046 B2 | 1/2004 | Hosheimer |
| 6,690,974 B2 | 2/2004 | Archer et al. |
| 6,697,676 B2 | 2/2004 | Dahl et al. |
| 6,714,822 B2 | 3/2004 | King et al. |
| 6,837,886 B2 | 1/2005 | Collins et al. |
| 6,842,648 B2 | 1/2005 | Partridge et al. |
| 6,895,283 B2 | 5/2005 | Erickson et al. |
| 6,909,918 B2 | 6/2005 | Stypulkowski |
| 6,959,820 B2 | 11/2005 | Koslow |
| 6,988,007 B1 | 1/2006 | Morgan |
| 6,999,820 B2 | 2/2006 | Jordan |
| 7,072,719 B2 | 7/2006 | Vinup et al. |
| 7,177,702 B2 | 2/2007 | Wallace et al. |

| | | | |
|---|---|---|---|
| 7,231,260 | B2 | 6/2007 | Wallace et al. |
| 7,349,743 | B2 | 3/2008 | Tadlock |
| 7,561,924 | B2 * | 7/2009 | Kolberg et al. ............... 607/123 |
| 7,590,454 | B2 | 9/2009 | Garabedian et al. |
| 2001/0025192 | A1 | 9/2001 | Gerber et al. |
| 2001/0041821 | A1 | 11/2001 | Wilk |
| 2001/0053885 | A1 | 12/2001 | Gielen et al. |
| 2002/0026228 | A1 | 2/2002 | Schauerte |
| 2002/0111661 | A1 | 8/2002 | Cross et al. |
| 2002/0151948 | A1 | 10/2002 | King et al. |
| 2002/0151949 | A1 | 10/2002 | Dahl et al. |
| 2002/0156513 | A1 | 10/2002 | Borkan |
| 2002/0183791 | A1 | 12/2002 | Denker et al. |
| 2002/0188207 | A1 | 12/2002 | Richter |
| 2003/0014016 | A1 | 1/2003 | Purdy |
| 2003/0040785 | A1 | 2/2003 | Maschino et al. |
| 2003/0097051 | A1 | 5/2003 | Kolberg et al. |
| 2003/0199962 | A1 | 10/2003 | Struble et al. |
| 2003/0204135 | A1 | 10/2003 | Bystritsky |
| 2003/0204228 | A1 | 10/2003 | Cross, Jr. et al. |
| 2004/0015193 | A1 | 1/2004 | Lamson et al. |
| 2004/0098074 | A1 | 5/2004 | Erickson et al. |
| 2005/0004639 | A1 | 1/2005 | Erickson |
| 2005/0137646 | A1 | 6/2005 | Wallace et al. |
| 2005/0149156 | A1 | 7/2005 | Libbus et al. |
| 2005/0203599 | A1 | 9/2005 | Garabedian et al. |
| 2005/0203600 | A1 | 9/2005 | Wallace et al. |
| 2005/0203602 | A1 | 9/2005 | Wallace et al. |
| 2005/0251238 | A1 | 11/2005 | Wallace et al. |
| 2005/0251239 | A1 | 11/2005 | Wallace et al. |
| 2006/0129203 | A1 | 6/2006 | Garabedian et al. |
| 2006/0161246 | A1 | 7/2006 | Rhim et al. |
| 2006/0259110 | A1 | 11/2006 | Wallace et al. |

FOREIGN PATENT DOCUMENTS

| | | |
|---|---|---|
| EP | 0865800 A2 | 9/1998 |
| EP | 0865800 A3 | 12/1999 |
| EP | 0865800 B1 | 9/2004 |
| WO | WO 01/85094 | 11/2001 |
| WO | WO 03/077986 | 9/2003 |

OTHER PUBLICATIONS

Extended European Search Report dated Dec. 19, 2008 in EP Application No. 08017295.0-1265; (5 pages).
Office Action dated Aug. 30, 2007 for related European Patent Application No. 05733553.1-1265, Applicant: Boston Scientific Limited (4 pages).
Non-Final Office Action dated Aug. 23, 2005 in U.S. Appl. No. 10/799,270, filed Mar. 12, 2004, Inventor: Michael P. Wallace, (15 pages).
Non-Final Office Action dated Jan. 9, 2006 in U.S. Appl. No. 10/799,270, filed Mar. 12, 2004, Inventor: Michael P. Wallace, (13 pages).
Notice of Allowance dated Oct. 11, 2006 in U.S. Appl. No. 10/799,270, filed Mar. 12, 2004, Inventor: Michael P. Wallace, (11 pages).
Non-Final Office Action dated Sep. 19, 2005 in U.S. Appl. No. 10/799,295, filed Mar. 12, 2004, Inventor: Michael P. Wallace, (10 pages).
Final Rejection dated Mar. 2, 2006 in U.S. Appl. No. 10/799,295, filed Mar. 12, 2004, Inventor: Michael P. Wallace, (10 pages).
Advisory Action dated Jul. 5, 2006 in U.S. Appl. No. 10/799,295, filed Mar. 12, 2004, Inventor: Michael P. Wallace, (3 pages).
Non-Final Office Action dated Oct. 2, 2009 in U.S. Appl. No. 11/459,618, filed Jul. 24, 2006, Inventor: Michael P. Wallace, (18 pages).
Final Office Action dated Apr. 13, 2010 in U.S. Appl. No. 11/459,618, filed Jul. 24, 2006, Inventor: Michael P. Wallace, (9 pages).
Non-Final Office Action dated Feb. 15, 2011 in U.S. Appl. No. 11/459,618, filed Jul. 24, 2006, Inventor: Michael P. Wallace, (21 pages).
Non-Final Office Action dated Nov. 2, 2005 in U.S. Appl. No. 10/841,069, filed May 6, 2004, Inventor: Michael P. Wallace, (10 pages).
Final Rejection dated May 4, 2006 in U.S. Appl. No. 10/841,069, filed May 6, 2004, Inventor: Michael P. Wallace, (9 pages).
Final Rejection dated Mar. 25, 2008 in U.S. Appl. No. 10/841,069, filed May 6, 2004, Inventor: Michael P. Wallace, (10 pages).
Advisory Action dated Jun. 4, 2008 in U.S. Appl. No. 10/841,069, filed May 6, 2004, Inventor: Michael P. Wallace, (6 pages).
Final Rejection dated Nov. 28, 2008 in U.S. Appl. No. 10/841,069, filed May 6, 2004, Inventor: Michael P. Wallace, (19 pages).
Advisory Action dated Feb. 10, 2009 in U.S. Appl. No. 10/841,069, filed May 6, 2004, Inventor: Michael P. Wallace, (3 pages).
Non-Final Rejection dated May 12, 2009 in U.S. Appl. No. 10/841,069, filed May 6, 2004, Inventor: Michael P. Wallace, (14 pages).
Final Office Action dated Dec. 8, 2009 in U.S. Appl. No. 10/841,069, filed May 6, 2004, Inventor: Michael P. Wallace, (14 pages).
Non-Final Office Action dated Jun. 7, 2006 in U.S. Appl. No. 10/841,070, filed May 6, 2004, Inventor: Michael P. Wallace, (13 pages).
Notice of Allowance dated Jan. 12, 2007 in U.S. Appl. No. 10/841,070, filed May 6, 2004, Inventor: Michael P. Wallace, (6 pages).
Notice of Allowance dated Apr. 5, 2007 in U.S. Appl. No. 10/841,070, filed May 6, 2004, Inventor: Michael P. Wallace, (8 pages).
Non-Final Office Action dated May 25, 2006 in U.S. Appl. No. 10/799,271, filed Mar. 12, 2004, Inventor: Robert J. Garabedian, (15 pages).
Non-Final Office Action dated Jun. 26, 2007 in U.S. Appl. No. 10/799,271, filed Mar. 12, 2004, Inventor: Robert J. Garabedian, (11 pages).
Final Rejection dated Nov. 5, 2007 in U.S. Appl. No. 10/799,271, filed Mar. 12, 2004, Inventor: Robert J. Garabedian, (8 pages).
Non-Final Rejection dated Apr. 16, 2008 in U.S. Appl. No. 10/799,271, filed Mar. 12, 2004, Inventor: Robert J. Garabedian, (22 pages).
Non-Final Office Action dated Oct. 21, 2008 in U.S. Appl. No. 10/799,271, filed Mar. 12, 2004, Inventor: Robert J. Garabedian, (9 pages).
Notice of Allowance dated May 19, 2009 in U.S. Appl. No. 10/799,271, filed Mar. 12, 2004, Inventor: Robert J. Garabedian, (7 pages).
Non-Final Office Action dated Jan. 8, 2008 in U.S. Appl. No. 11/010,232, filed Dec. 10, 2004, Inventor: Robert J. Garabedian, (18 pages).
Final Rejction dated Jun. 18, 2008 in U.S. Appl. No. 11/010,232, filed Dec. 10, 2004, Inventor: Robert J. Garabedian, (10 pages).
Advisory Action dated Sep. 2, 2008 in U.S. Appl. No. 11/010,232, filed Dec. 10, 2004, Inventor: Robert J. Garabedian, (5 pages).
Final Office Action dated Feb. 13, 2009 in U.S. Appl. No. 11/010,232, filed Dec. 10, 2004, Inventor: Robert J. Garabedian, (12 pages).
Advisory Action dated May 6, 2009 in U.S. Appl. No. 11/010,232, filed Dec. 10, 2004, Inventor: Robert J. Garabedian, (3 pages).
Non-Final Office Action dated Aug. 5, 2009 in U.S. Appl. No. 11/010,232, filed Dec. 10, 2004, Inventor: Robert J. Garabedian, (14 pages).
Final Office Action dated Mar. 2, 2010 in U.S. Appl. No. 11/010,232, filed Dec. 10, 2004, Inventor: Robert J. Garabedian, (12 pages).
Final Office Action dated May 25, 2010 in U.S. Appl. No. 11/010,232, filed Dec. 10, 2004, Inventor: Robert J. Garabedian, (11 pages).
Advisory Action dated Jul. 30, 2010 in U.S. Appl. No. 11/010,232, filed Dec. 10, 2004, Inventor: Robert J. Garabedian, (6 pages).
Notice of Allowance dated Dec. 23, 2010 in U.S. Appl. No. 11/010,232, filed Dec. 10, 2004, Inventor: Robert J. Garabedian, (8 pages).
PCT Written Opinion of the International Search Authority for PCT/US/2005/006569, Applicant: Boston Scientific Scimed, Inc., Form PCT/ISA/237, dated Jun. 13, 2005 (5 pages).
PCT International Search Report for PCT/US/2005/006569, Applicant: Boston Scientific Scimed, Inc., Form PCT/ISA/237, dated Jun. 13, 2005 (7 pages).
PCT International Search Report for PCT/US2005/010121, Applicant: Boston Scientific Scimed, Inc., Form PCT/ISA/210 and 220, dated Jun. 13, 2005 (7 pages).

PCT Written Opinion of the International Search Authority for PCT/US/2005/010121, Applicant: Boston Scientific Scimed, Inc., Form PCT/ISA/237, dated Jul. 4, 2005 (5 pages).

Canavero, Sergio et al., "Extradural Motor Cortex Stimulation for Advanced Parkinson Disease," J. Neurosurg. 97: pp. 1208-1211, 2002.

Kunieda, Takeharu et al., "Use of Cavernous Sinus EEG in the Detection of Seizure Onset and Spread in Mesial Temporal Lobe Epilepsy," Epilepsia, 41(11): pp. 1411-1419, 2000.

Onal, Cagatay, et al. "Complications of Invasive Subdural Grid Monitoring in Children with Epilepsy," J. Neurosurg. 98: pp. 1017-1026, 2003.

Final Office Action dated Oct. 31, 2007 for related U.S. Appl. No. 10/841,070, Inventor: Michael Wallace et al. (15 pages).

Advisory Action dated Aug. 11, 2006 for related U.S. Appl. No. 10/841,069, Inventor: Michael P. Wallace et al. (3 pages).

Advisory Action dated Sep. 13, 2006 for related U.S. Appl. No. 10/841,069, Inventor: Michael P. Wallace et al. (3 pages).

Advisory Action dated Dec. 6 2006 for related U.S. Appl. No. 10/841,069, Inventor: Michael P. Wallace et al. (3 pages).

Non-Final Office Action dated Jun. 15, 2007 for related U.S. Appl. No. 10/841,069, Inventor: Michael P. Wallace et al. (8 pages).

Office Action dated Apr. 10, 2007 for related U.S. Appl. No. 11/010,232, Inventor: Robert J. Garabedian et al. (9 pages).

Final Office Action dated Aug. 22, 2007 for related U.S. Appl. No. 11/010,232, Inventor: Robert J. Garabedian et al. (8 pages).

IP.com: Electrode Design to Stimulate Blood Vessels, Nerves, or Other Tubular Organs, file://C:\unzipped\IPCOM000010247D1\0_properties.xml, Published Nov. 13, 2002.

IP.com: Epidural Needle for Spinal Cord Stimulation Electrode, file://C:\unzipped\IPCOM000011384D1\0_properties.xml, Published Feb. 14, 2003.

IP.com: Medical Lead System and Method for Insertion into the Spinal Cord, file://C:\unzipped\IPCOM000011389D1\0_properties.xml, Published Feb. 17, 2003.

IP.com: Transcutaneous Screening Test for Evaluation of Potential Efficacy of Chronic Trigeminal Neurostimulation as a Therapy for Epilepsy, file://C:\unzipped\IPCOM000011987D1\0_properties.xml, Published Mar. 28, 2003.

IP.com: System and Method for Lead Fixation, file://C:\unzipped\IPCOM000019571D1\0_properties.xml, Published Sep. 19, 2003.

IP.com: Dual Lumen Inflatable Lead, file://C:\unzipped\IPCOM000019703D1\0_properties.xml, Published Sep. 25, 2003.

IP.com: Skull-Mounted Electrical Stimulation System, file://C:\unzipped\IPCOM000019827D1\0_properties.xml, Published Oct. 1, 2003.

IP.com: Spinal Cord Stimulation as a Therapy for Epilepsy, file://C:\unzipped\IPCOM000019881D1\0_properties.xml, Published Oct. 6, 2003.

IP.com: Skull-Mounted Electrical Stimulation System and Method for Treating Patients, file://C:\unzipped\IPCOM000021554D1\0_properties.xml, Published Jan. 22, 2004.

Web Article: IP.com: Methods and Placement of Neurostimulation Lead, Infusion Catheter, and/or Sensor Via the Vasculature to the Brain, file://C:\unzipped\IPCOM000012135D1\0_properties.xml, Published Apr. 10, 2003.

Web Article: IP.com: Methods and Placement of Neurostimulation Lead, Infusion Catheter, and/or Sensor Via Peripheral Vasculature, 0349945-003. (7 pages).

PCT International Search Report for PCT/US2005/007179, Applicant: Boston Scientific Scimed, Inc., Forms PCT/ISA/210 and 220, dated Jun. 24, 2005 (6 pages).

PCT Written Opinion of the International Search Authority for PCT/US2005/007179, Applicant: Boston Scientific Scimed, Inc., Form PCT/ISA/237, dated Jun. 24, 2005 (5 pages).

* cited by examiner

MODULAR STIMULATION LEAD NETWORK

RELATED APPLICATIONS

The present application is a continuation of U.S. patent application Ser. No. 10/799,271, filed Mar. 12, 2004, which application is herein incorporated by reference in its entirety.

FIELD OF THE INVENTION

The invention relates to the implantation of stimulation leads within a patient, and in particular, the implantation of electrode leads within a patient's spine to treat disorders, such as chronic pain.

BACKGROUND OF THE INVENTION

It is known to treat chronic pain by electrically stimulating the spinal cord, spinal nerve roots, and other nerve bundles. Although not fully understood, the application of electrical energy to particular regions of the spinal cord induces parasthesia (i.e., a subjective sensation of numbness or tingling) in the afflicted body regions associated with the stimulated spinal regions. This parasthesia effectively masks the transmission of chronic pain sensations from the afflicted body regions to the brain. Since each body region is associated with a particular spinal nerve root, it is important that stimulation be applied at the proper longitudinal position along the spinal cord to provide successful pain management and avoid stimulation of unaffected regions of the body. Also, because nerve fibers extend between the brain and the nerve roots along the same side of the spine as the body regions they control, it is equally important that stimulation be applied at the proper lateral position of the spinal cord. For example, to treat unilateral pain (i.e., pain sensed only on one side of the body), electrical stimulation is applied to the corresponding side of the spinal cord. To treat bilateral pain (i.e., pain sensed on both sides of the body), electrical stimulation is either applied directly to the midline of the spinal cord or applied to both lateral sides of the spinal cord.

In a typical procedure, one or more stimulation leads are introduced through the patient's back into the epidural space under fluoroscopy. The specific procedure used to implant the stimulation lead will ultimately depend on the type of stimulation lead used. Currently, there are two types of commercially available stimulation leads: a percutaneous lead and a surgical lead.

A percutaneous lead comprises a cylindrical body with ring electrodes, and can be introduced into contact with the affected spinal tissue through a Touhy-like needle, which passes through the skin, between the desired vertebrae, and into the spinal cavity above the dura layer. For unilateral pain, a percutaneous lead is placed on the corresponding lateral side of the spinal cord. For bilateral pain, a percutaneous lead is placed down the midline of the spinal cord, or two percutaneous leads are placed down the respective sides of the midline.

A surgical lead has a paddle on which multiple electrodes are arranged in independent columns, and is introduced into contact with the affected spinal tissue using a surgical procedure, and specifically, a laminectomy, which involves removal of the laminar vertebral tissue to allow both access to the dura layer and positioning of the lead.

After the stimulation lead(s) (whether percutaneous or surgical) are placed at the target area of the spinal cord, the lead(s) are anchored in place, and the proximal ends of the lead(s), or alternatively lead extensions, are passed through a tunnel leading to a subcutaneous pocket (typically made in the patient's abdominal area) where a neurostimulator is implanted. The lead(s) are connected to the neurostimulator, which is then operated to test the effect of stimulation and adjust the parameters of the stimulation for optimal pain relief. During this procedure, the patient provides verbal feedback regarding the presence of paresthesia over the pain area. Based on this feedback, the lead position(s) may be adjusted and re-anchored if necessary. Any incisions are then closed to fully implant the system.

Various types of stimulation leads (both percutaneous and surgical), as well as stimulation sources and other components, for performing spinal cord stimulation are commercially available from Medtronic, Inc., located in Minneapolis, Minn., and Advanced Neuromodulation Systems, Inc., located in Plano, Tex.

The use of surgical leads provides several functional advantages over the use of percutaneous leads. For example, the paddle on a surgical leads has a greater footprint than that of a percutaneous lead. As a result, an implanted surgical lead is less apt to migrate from its optimum position than is an implanted percutaneous lead, thereby providing a more efficacious treatment and minimizing post operative procedures otherwise required to reposition the lead. As another example, the paddle of a surgical lead is insulated on one side. As a result, almost all of the stimulation energy is directed into the targeted neural tissue. The electrodes on the percutaneous leads, however, are entirely circumferentially exposed, so that much of the stimulation energy is directed away from the neural tissue. This ultimately translates into a lack of power efficiency, where percutaneous leads tend to exhaust a stimulator battery supply 25%-50% greater than that exhausted when surgical leads are used. As still another example, the multiple columns of electrodes on a surgical lead are well suited to address both unilateral and bilateral pain, where electrical energy may be administered using either column independently or administered using both columns.

Although surgical leads are functionally superior to percutaneous leads, there is one major drawback—surgical leads require painful surgery performed by a neurosurgeon, whereas percutaneous leads can be introduced into the epidural space minimally invasively by an anesthesiologist using local anesthesia.

There, thus, remains a need for a minimally invasive means of introducing stimulation leads within the spine of a patient, while preserving the functional advantages of a surgical lead.

SUMMARY OF THE INVENTION

Although the present inventions should not be so limited in their broadest aspects, they lend themselves well to medical applications, wherein access to a target site must be made through a limited opening, yet the resulting medical platform used to perform a medical procedure at such target site is larger than the access opening. The present inventions lend themselves particularly well to the percutaneous installation and subsequent operation of a stimulation lead assembly within the epidural space of a patient to treat ailments, such as chronic pain.

In accordance with a first aspect of the present inventions, a stimulation kit comprising first and second tissue stimulation leads is provided. The first stimulation lead comprises a first elongated body, a first stimulation element (e.g., an electrode), and a first coupling mechanism longitudinally extending along at least a portion of the first elongated body. The second stimulation lead comprises a second elongated body, a second stimulation element (e.g., an electrode), and a first complementary coupling mechanism configured to slidably engage the first coupling mechanism, e.g., in a rail and slot arrangement. The stimulation kit may optionally comprise a stimulation source configured to be coupled to the first and second stimulation leads. Optionally, each of the stimulation leads comprises a plurality of stimulation elements in order to provide a more extensive stimulation coverage.

In one embodiment, the first and second elongated bodies are cylindrically-shaped, although other shapes are possible depending on the particular application. The size of the elongated bodies can be any size that is consistent with the stimulation procedure in which the stimulation leads will be employed. Although, for medical procedures, such as spinal cord stimulation, the greatest cross-sectional dimension of at least one of the elongated bodies is preferably 5 mm or less in order to minimize the size of the opening through which the stimulation leads will be introduced. The elongated bodies can have the same length, or alternatively, one elongated body can be shorter than the other, such that, e.g., the shorter elongated body can be entirely delivered within the patient's body without any portion extending from the access opening. In one embodiment, the stimulation elements of the respective stimulation leads face the same direction, e.g., to focus the stimulation energy in one direction.

The stimulation elements may be mounted directly on the elongated bodies, or alternatively, may be mounted to some other element of the stimulation leads. For example, the second stimulation lead may have a flap on which the respective stimulation element is disposed. In this case, the flap may extend along a portion of the complementary coupling mechanism, so that it can be secured by the coupling mechanism of the first stimulation lead when the portion of the complementary coupling mechanism slidably engages the coupling mechanism of the first stimulation lead and released by the coupling mechanism of the first stimulation lead when the portion of the complementary coupling mechanism slidably disengages the coupling mechanism of the first stimulation lead.

In one embodiment, the distal end of the second elongated body is configured to be in close contact with the first elongated body when engaging each other. Alternatively, the first elongated body is configured to deploy from the first elongated body by slidably disengaging at least a portion of the complementation coupling mechanism from the coupling mechanism of the first stimulation lead. In this case, the distal end of the second elongated body can be pre-curved to provide it with a predefined configuration. Optionally, the second elongated body may be configured to be actively changed from a first geometry to a second geometry after deployment from the first elongated body. For example, the kit may comprise a stylet configured to be introduced through the second elongated body to change the second elongated body from the first geometry to the second geometry. Or the secondary stimulation lead may comprise a pullwire configured to be pulled to change the second elongated body from the first geometry to the second geometry.

The kit may have more than two stimulation leads. For example, the first stimulation lead may comprise another coupling mechanism longitudinally extending along at least a portion of the respective elongated body, in which case, the kit may further comprise a third stimulation lead comprising an elongated body, a stimulation element mounted on the elongated body, and another complementary coupling mechanism configured to slidably engage the other coupling mechanism of the first stimulation lead.

In one preferred method of using the stimulation kit to treat a disorder (e.g., chronic pain) in a patient, the first stimulation lead is delivered into the epidural space of the patient's spine, and the second stimulation lead is delivered into the epidural space by sliding the complementary coupling mechanism along the coupling mechanism of the first stimulation lead. Stimulation energy can then be conveyed from the stimulation elements into the neural tissue.

Preferably, the first and second stimulation leads are delivered through a percutaneous opening within the patient's skin, thereby minimizing patient discomfort and damage to otherwise healthy tissue. Although delivered in a minimally invasive manner, the larger footprint created by the coupled stimulation leads provides the assembly with more stability and greater coverage area. Thus, although not necessarily limited in its broadest aspects, the advantages of a surgical lead are retained by the present invention, without the disadvantages associated with invasive surgical procedures otherwise required to implant surgical leads.

In accordance with a second aspect of the present inventions, a method of treating a disorder (e.g., chronic pain) is provided. The method comprises delivering a first stimulation lead into the epidural space of the patient's spine, and delivering a second stimulation lead into the epidural space by slidably engaging the second stimulation lead along the first stimulation lead. A third stimulation lead can optionally be delivered into the epidural space by slidably engaging the third stimulation lead along the first stimulation lead. In one preferred method, the stimulation leads are delivered into the epidural space through a percutaneous opening. For example, the first stimulation lead can be introduced through a delivery device into the epidural space, and then the second stimulation lead can be delivered along the first stimulation lead.

In one preferred method, the stimulation leads are coupled to a stimulation source, in which case, the method may further comprise conveying stimulation energy (e.g., electrical energy) from the stimulation source to the stimulation leads to stimulate neural tissue within the patient's spine. The stimulation energy may be focused into the neural tissue, as opposed to conveying the stimulation energy in all radial directions. In the preferred method, the stimulation leads are implanted within the patient's spine, e.g., to provide extended relief.

In accordance with a third aspect of the present inventions, a medical kit is provided. The medical kit is similar to the previously described stimulation kit, with the exception that the medical kit comprises first and second medical leads with respective operative elements that are not limited to stimulation elements, but rather can be any elements that are capable of performing a medical function within a targeted tissue region.

In accordance with a fourth aspect of the present inventions, a method of performing a medical procedure on a patient is provided. This method is similar to the previously described method, with the exception that it is not limited to stimulation of tissue within the epidural space of the patient.

In accordance with a fifth aspect of the present inventions, a stimulation kit is provided. The stimulation kit is similar to the previously described stimulation kit, with the exception that it comprises a guide and a stimulation lead. The guide is similar to the first stimulation lead of the previously described stimulation kit, with the exception that it need not have a stimulation element.

In accordance with a sixth aspect of the present inventions, a medical kit is provided. The medical kit is similar to the previously described medical kit, with the exception that it comprises a guide and a medical lead. The guide is similar to the first medical lead of the previously described medical kit, with the exception that it need not have an operative element.

BRIEF DESCRIPTION OF THE DRAWINGS

The drawings illustrate the design and utility of preferred embodiment(s) of the invention, in which similar elements are referred to by common reference numerals. In order to better appreciate the advantages and objects of the invention, reference should be made to the accompanying drawings that illustrate the preferred embodiment(s). The drawings, however, depict the embodiment(s) of the invention, and should not be taken as limiting its scope. With this caveat, the embodiment(s) of the invention will be described and explained with additional specificity and detail through the use of the accompanying drawings in which:

FIG. 15a is a cross-sectional view of the stimulation lead assembly of FIG. 14a, taken along the line 15a-15a;

DETAILED DESCRIPTION OF THE PREFERRED EMBODIMENTS

Figure 1:
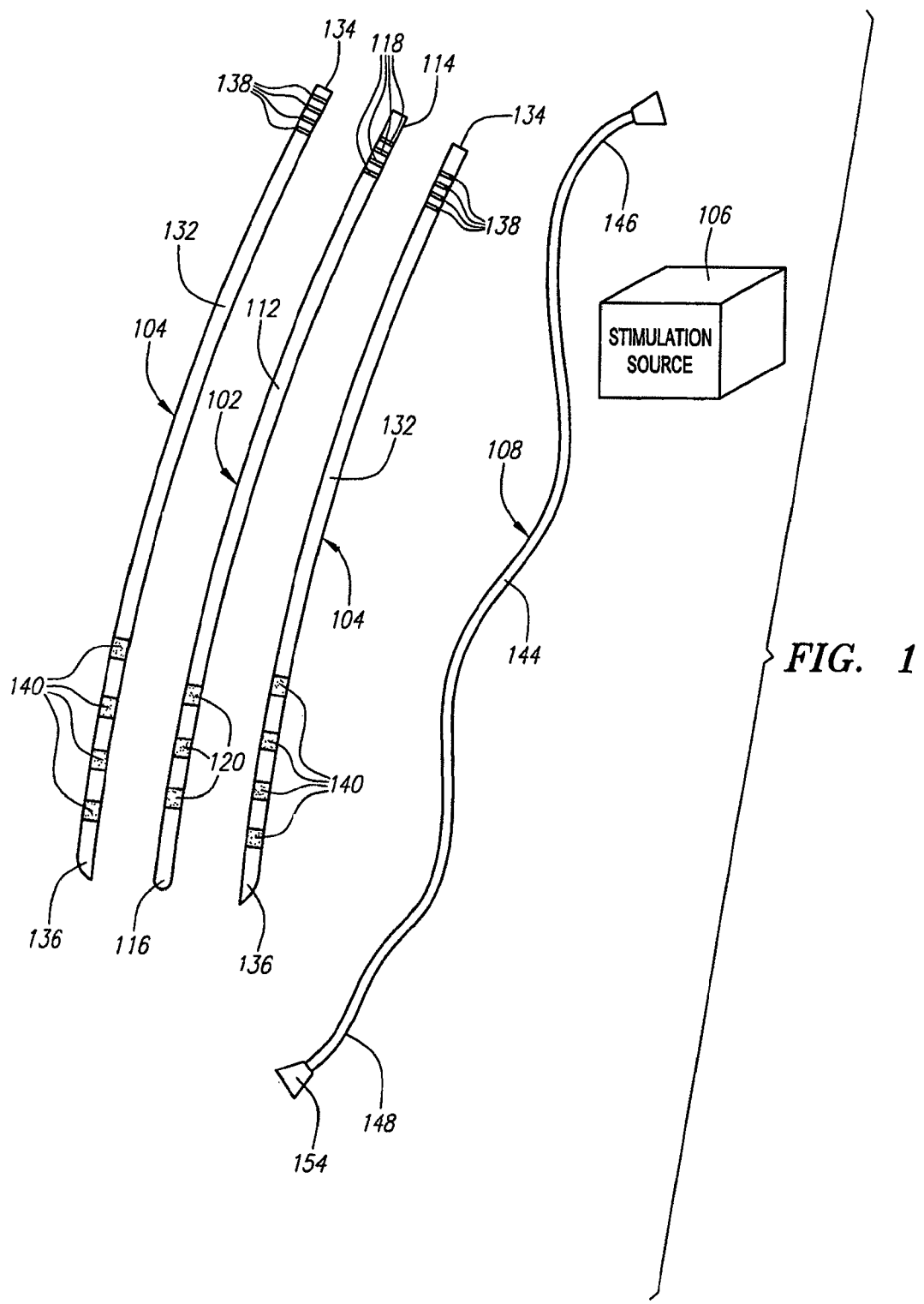
FIG. 1 is a plan view of a modular stimulation lead kit arranged in accordance with a preferred embodiment of the present invention.
Figure 2:
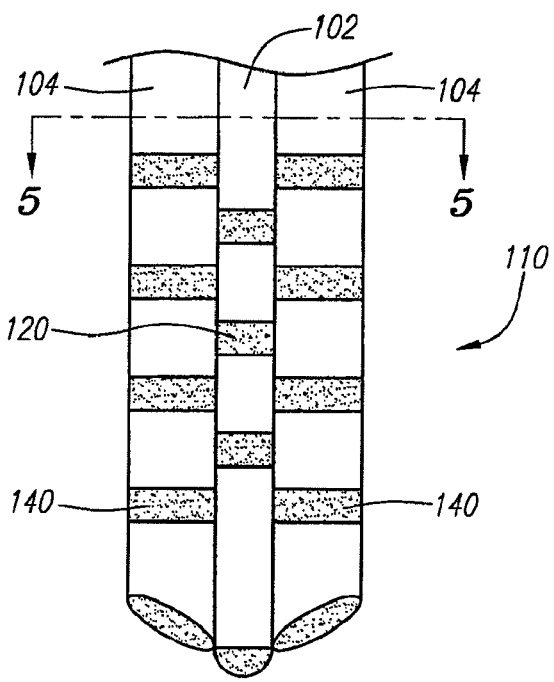
FIG. 2 is a cutaway top view of a stimulation lead assembly formed from the kit of FIG. 1.

Referring now to FIG. 1, a modular stimulation lead kit 100 arranged in accordance with one preferred embodiment of the present invention is shown. In its simplest form, the stimulation kit 100 generally comprises a primary stimulation lead 102 and two secondary stimulation leads 104, which are configured to be percutaneously delivered and implanted into the epidural space of a patient's spine, an implantable electrical stimulation source 106 configured for delivering stimulation energy to the stimulation leads 102/104, and an optional extension lead 108 configured for connecting the stimulation leads 102/104 to the remotely implanted stimulation source 106. As will be described in further detail below, the secondary stimulation leads 104 can be attached to the primary stimulation lead 102 to form a modularized stimulation lead assembly 110, as illustrated in FIG. 2.

It should be noted that although the kit 100 illustrated in FIG. 1 is described herein as being used in spinal cord stimulation (SCS) for the treatment of chronic pain, the kit 100, or a modification of the kit 100, can be used in an SCS procedure to treat other ailments, or can used in other applications other than SCS procedures, such as peripheral nervous system stimulation, sacral root stimulation, and brain tissue stimulation, including cortical and deep brain stimulation. In the latter case, the stimulation leads 102/104 can be delivered through a miniature cranial burr hole into the brain tissue.

The primary stimulation lead 102 comprises an elongated sheath body 112 having a proximal end 114 and a distal end 116. The sheath body 112 is composed of a suitably flexible material (such as polyurethane, silicone, etc.), which may either be resilient or non-resilient, and may be formed via an extrusion process or by any other suitable means. The distal end 116 of the sheath body 112 is soft and tapered to prevent injury to nerve roots that exit the spinal cord when delivered into the epidural space of the patient's spine. In the illustrated embodiment, the sheath body 112 is cylindrically-shaped and sized to fit through a Touhy-like needle (not shown). In this case, the diameter of the sheath body 112 is preferably less than 5 mm to allow it to be percutaneously introduced through a needle. More preferably, the diameter of the sheath body 112 is within the range of 1 mm to 3 mm, so that the primary stimulation lead 102, along with the secondary stimulation leads 104 described below, can comfortably fit within the epidural space of the patient. The sheath body 112 may have other cross-sectional geometries, such as elliptical, rectangular, triangular, etc. If rectangular, the width of the primary stimulation lead 102 can be up to 5 mm, since the width of an epidural space is greater than its height. The sheath body 112 may have an optional lumen (not shown) for receiving a stylet (not shown) that axially stiffens the sheath body 112 to facilitate percutaneous introduction of the primary stimulation lead 102 within the epidural space of the patient's spine, as will be described in further detail below.

The primary stimulation lead 102 further comprises a plurality of terminals 118 (in this case, three) mounted on the proximal end 114 of the sheath body 112, and a plurality of stimulation elements, and in particular electrodes 120 (in this case, three), mounted on the distal end 116 of the sheath body 112. The terminals 118 are formed of ring-shaped elements composed of a suitable biocompatible metallic material, such as platinum, platinum/iridium, stainless steel, gold, or combinations or alloys of these materials, and can be mounted to the sheath body 112 in an interference fit arrangement.

In the illustrated embodiment, the electrodes 120 are formed on one circumferential side of the sheath body 112 (shown best in FIG. 3) in order to focus stimulation energy in one direction, thereby maximizing energy efficiency. The electrodes 120 can be formed onto the sheath body 112 using known deposition processes, such as sputtering, vapor deposition, ion beam deposition, electroplating over a deposited seed layer, or a combination of these processes. Alternatively, the electrodes 120 can be formed onto the sheath body 112 as a thin sheet or foil of electrically conductive metal affixed to the wall of the sheath body 112. The electrodes 120 can be composed of the same electrically conductive and biocompatible material as the terminals 118, e.g., platinum, platinum/iridium, stainless steel, gold, or combinations or alloys of these materials.

The primary stimulation lead 102 further comprises a plurality of conductors 122 (shown in FIG. 3) extending through the sheath body 112 and connecting each electrode 120 with a respective terminal 118. The conductors 122 are composed of a suitably electrically conductive material that exhibits the desired mechanical properties of low resistance, corrosion resistance, flexibility, and strength.

Figure 4:
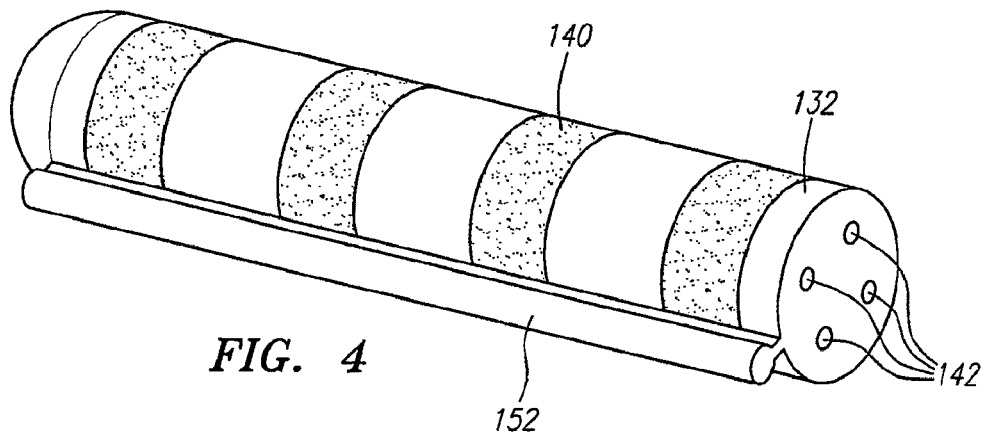
FIG. 4 is a cutaway perspective view of a secondary stimulation lead used in the kit of FIG. 1.

Like the primary stimulation lead 102, each secondary stimulation lead 104 comprises an elongated sheath body 132 having a proximal end 134 and a distal end 136, a plurality of terminals 138 (in this case, four) mounted to the proximal end 134 of the sheath body 132, a plurality of electrodes 140 (in this case, four) mounted to the distal end 136 of the sheath body 132, and a plurality of conductors 142 (shown in FIG. 4) extending through the sheath body 132 and respectively connecting the electrodes 120 to the terminals 118. The sheath bodies 132 of the secondary stimulation leads 104 are similar to the sheath body 112 of the primary stimulation lead 102, with the exception that the distal ends 136 are tapered in only one direction. In this manner, the stimulation lead assembly 110, as illustrated in FIG. 2, forms a lower profile distal end to facilitate placement of the assembly 110 within the epidural space of the patient's spine. Like the sheath body 112 of the primary stimulation lead 102, the sheath bodies 132 of the secondary stimulation leads 104 may each have an optional lumen (not shown) for receiving a stylet (not shown) to facilitate percutaneous introduction of the secondary stimulation lead 104 within the epidural space of the patient's spine, as will be described in further detail below.

Figure 3:
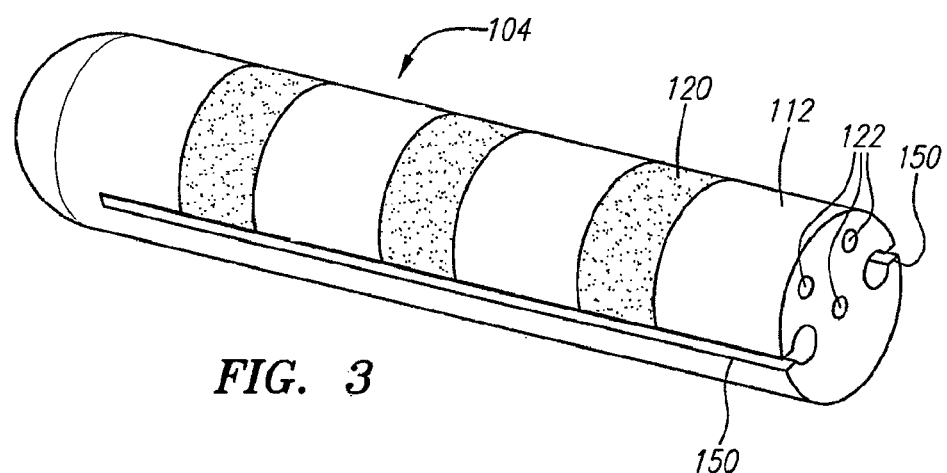
FIG. 3 is a cutaway perspective view of a primary stimulation lead used in the kit of FIG. 1.

The terminals 118 and electrodes 120 of the secondary stimulation leads 104 are similar to the terminals 118 and electrodes 120 of the primary stimulation lead 102, with the exception that there are four sets of terminals 118 and electrodes 120 instead of three. Notably, the electrodes 120 of the secondary stimulation leads 104 face the same direction as the electrodes 140 of the primary stimulation leads 102, so that the entire stimulation lead assembly 110 is capable of focusing electrical energy in a single direction, as shown in FIG. 3. Also, as illustrated in FIG. 3, the electrodes 120/140 are arranged on the respective sheath bodies 112/132, such that the electrodes 140 of the secondary stimulation leads 104 are offset from the electrodes 120 of the primary stimulation lead 102 in the longitudinal direction, thereby preventing accidental shorting between adjacent electrodes when the assembly 110 is formed.

Further details regarding the structure and composition of standard percutaneous stimulation leads are disclosed in U.S. Pat. No. 6,216,045, which is expressly incorporated herein by reference.

Figure 5:
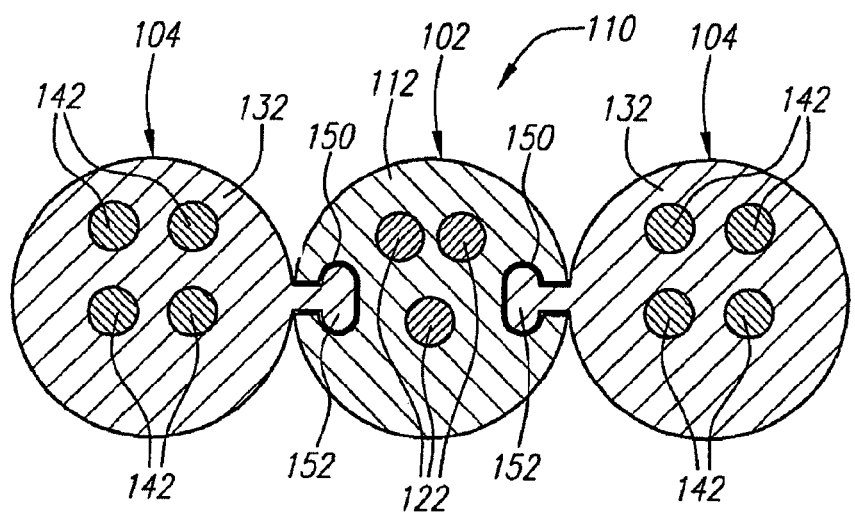
FIG. 5 is a cross-sectional view of the stimulation lead assembly of FIG. 2, taken along the line 5-5.

The primary stimulation lead 102 and the respective secondary stimulation leads 104 are configured to slidably engage each other to form the lead assembly 110 illustrated in FIG. 2. In particular, referring to FIGS. 3-5, the primary stimulation lead 102 comprises a pair of circumferentially opposed slots 150 extending along the length of the sheath body 112. The slots 150 can be formed in the sheath body 112 using any one of a variety of manners, but in the illustrated embodiment, the slots 150 are formed during the extrusion process. Alternatively, the slots 150 can be formed by embedding, or otherwise mounting, discrete slotted members (not shown) along the sheath body 112. In contrast, each of the secondary stimulation leads 104 comprises a rail 152 extending along the sheath body 132. Like the slots 150, the rail 152 can be formed on the sheath body 132 using any one of a variety of manners, such as forming the rail 152 during the extrusion process. Alternatively, the rail 152 can be formed of a discrete member (not shown) that is bonded, or otherwise mounted, to the sheath body 132. In other embodiments, the primary stimulation lead 102 may have a pair of circumferentially opposed rails extending along its sheath body 112, while the secondary stimulation leads 104 may have slots 150 extending along their sheath bodies 132. In any event, the rails 152 and slots 150 are sized to snuggly engage each other in a sliding relationship, as best shown in FIG. 5.

Thus, it can be appreciated that the secondary stimulation leads 104 can be coupled to the primary stimulation lead 102 by sliding the rails 152 of the respective secondary stimulation leads 104 along the respective slots 150 of the primary stimulation lead 102, thereby forming the stimulation assembly 110 illustrated in FIG. 2. The opposing slots 150 of the primary stimulation lead 102 and the rails 152 of the secondary stimulation leads 104 are circumferentially offset ninety degrees from the centers of the respective electrodes 120. In this manner, all of the electrodes 120, which generally face in the same direction, as described above, are ensured to face in a direction perpendicular to the plane of the assembly 110, thereby maximizing transmission of the stimulation energy into the target neural tissue when the assembly 110 is fully implanted within the epidural space of the patient's spine.

Although a rail and slot arrangement has been disclosed as the preferred means of slidably engaging the primary and stimulation leads 102/104, other means of slidably engaging the leads can be provided. For example, instead of slots, the primary stimulation lead can have loop structures (not shown) that extend along the opposing sides the respective sheath body. The secondary stimulation leads 104 can then be introduced through the respective sets of loop structures in order to couple the leads together.

Figure 13:
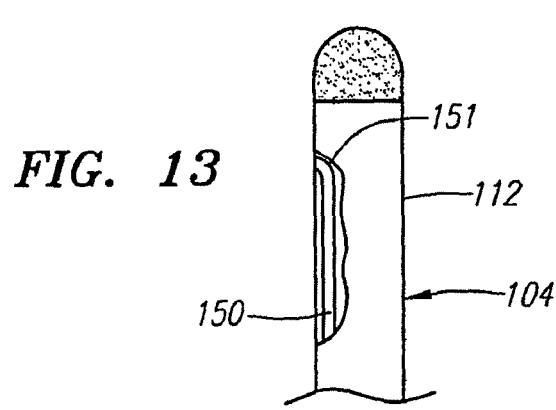
FIG. 13 is a partially cutaway top view of the distal end of an alternative primary stimulation lead that can be used in kit of FIG. 1.
Figure 14A:
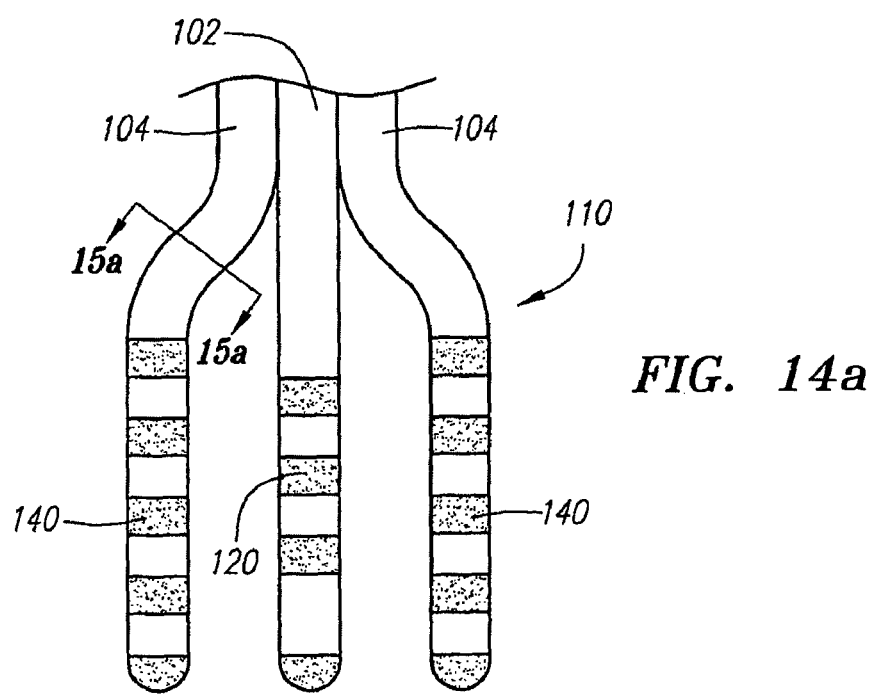
FIG. 14a is a cutaway top view of an alternative stimulation lead assembly that can be formed from the kit of FIG. 1 when the primary stimulation lead of FIG. 13 is used, wherein the secondary stimulation leads are shown in a normally curved geometry that converges towards the primary stimulation lead.

In the illustrated embodiment, the slots 150 have distal rail stops (not shown), i.e., the distal ends of the slots 150 terminate prior to the distal tip of the sheath body 112 to prevent the distal ends 136 of the secondary stimulation leads 104 from sliding distal to the distal end 116 of the primary stimulation lead 102. Alternatively, the distal ends of the slots 150 may have chamfered openings 151, as illustrated in FIG. 13. In this manner, the distal ends of the secondary stimulation leads 104 will diverge from the distal end of the primary stimulation lead 102 when the leads 102/104 are slidably engaged with each other. That is, when the rail 152 of a secondary stimulation lead 104 is slid along the respective slot 150 of the primary stimulation lead 102, the distal end of the rail 152 will be diverted out of the chamfered opening 151 at the distal end of the slot 150, thereby expanding the footprint of the resulting assembly 110, as illustrated in FIG. 14*a*. The secondary stimulation lead 104 may have a proximal rail stop (not shown) to prevent further sliding of the respective secondary stimulation lead 104 when fully deployed.

Figure 15A:
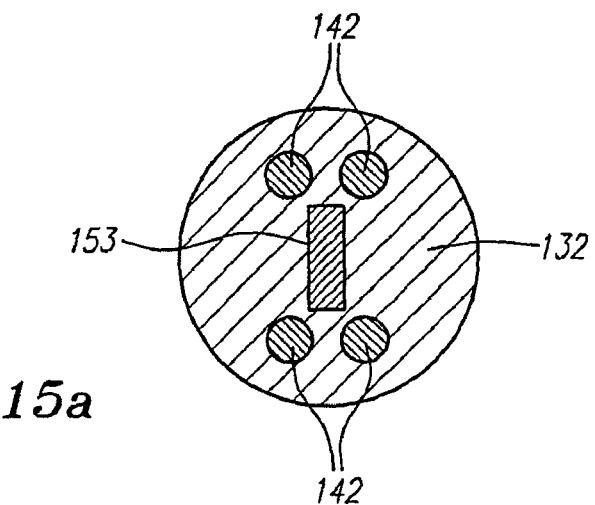

The distal ends of the secondary stimulation leads 104 can be pre-curved inward towards the primary stimulation lead 102, as illustrated in FIG. 14*a*, so that the distal ends of the secondary stimulation leads 104, when deployed from the primary stimulation lead 102, extend in a parallel direction with the distal end of the primary stimulation lead 102. The distal ends of the secondary stimulation leads 104 can be pre-curved in any one of a variety of manners. For example, as illustrated in FIG. 15*a*, a pre-curved resilient member 153 composed of a suitable material, such as nitinol, can be formed within the sheath body 132. Preferably, the cross-section of the resilient member 153 resembles of flat plate, so that the sheath body 132 consistently bends in a pre-defined plane, i.e., within the plane of the assembly 110.

Figure 14B:
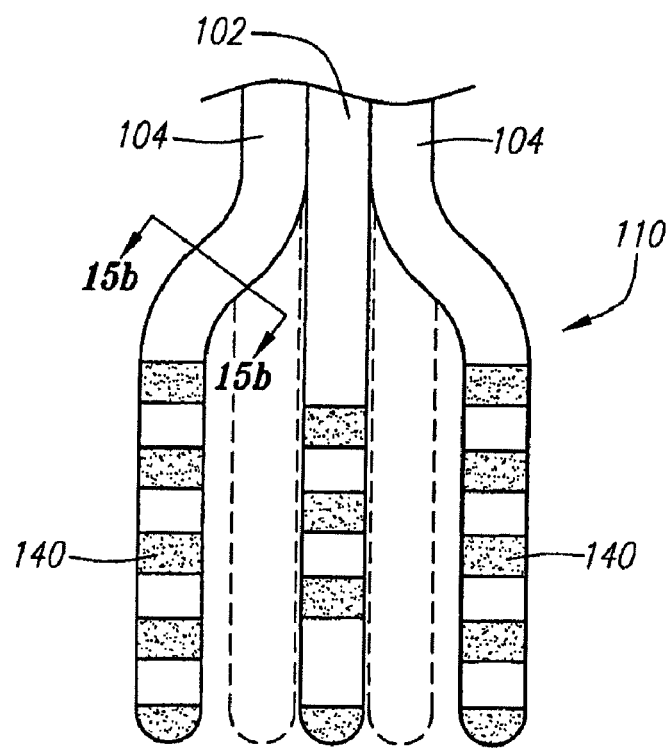
FIG. 14b is a cutaway top view of an alternative stimulation lead assembly that can be formed from the kit of FIG. 1 when the primary stimulation lead of FIG. 13 is used, wherein the secondary stimulation leads can be placed into a curved geometry that converges towards the primary stimulation lead when a stylet is introduced.
Figure 15B:
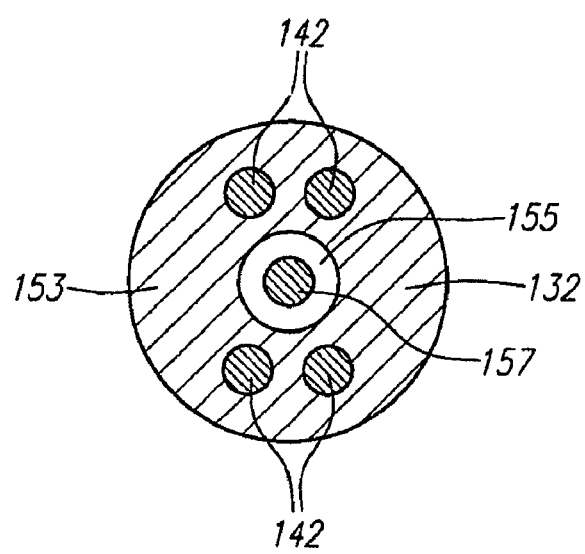
FIG. 15b is a cross-sectional view of the stimulation lead assembly of FIG. 14b, taken along the line 15b-15b.

Alternatively, as illustrated in FIG. 14*b*, the distal ends of the secondary stimulation leads 104 are not pre-curved, but rather normally exhibit a straight geometry after exiting slot 150 of the primary stimulation lead 102 (shown in phantom in FIG. 14*b*), such that the distal ends of the secondary stimulation leads 104 diverge from the primary stimulation lead 102. Alternatively, the distal ends of the secondary stimulation leads 104 may not be resilient. In either case, the secondary stimulation lead 104 comprises a lumen 155 through which a curved stylet 157 is introduced, as illustrated in FIG. 15*b*. The distal end of the stylet 157 is curved, such that, when introduced through the lumen 155, the distal end of the respective stimulation lead 104 assumes a geometry that curves inward towards the primary stimulation lead 102, as illustrated in FIG. 14*b*. Differently curved stylets 157 can be used in order to provide the distal end of the secondary stimulation lead 104 with the desired curved geometry. Alternatively, rather than providing a curved stylet 157 and a normally straight secondary stimulation lead 104, the distal end of the secondary stimulation lead 104 can be pre-curved much like the stimulation lead 104 illustrated in FIG. 14*a*. In this case, the distal end of the stylet 157 can be straight, so that its introduction through the lumen 157 straightens the pre-curved distal end of the secondary stimulation lead 104, as shown in phantom in FIG. 14*b*.

Figure 14C:
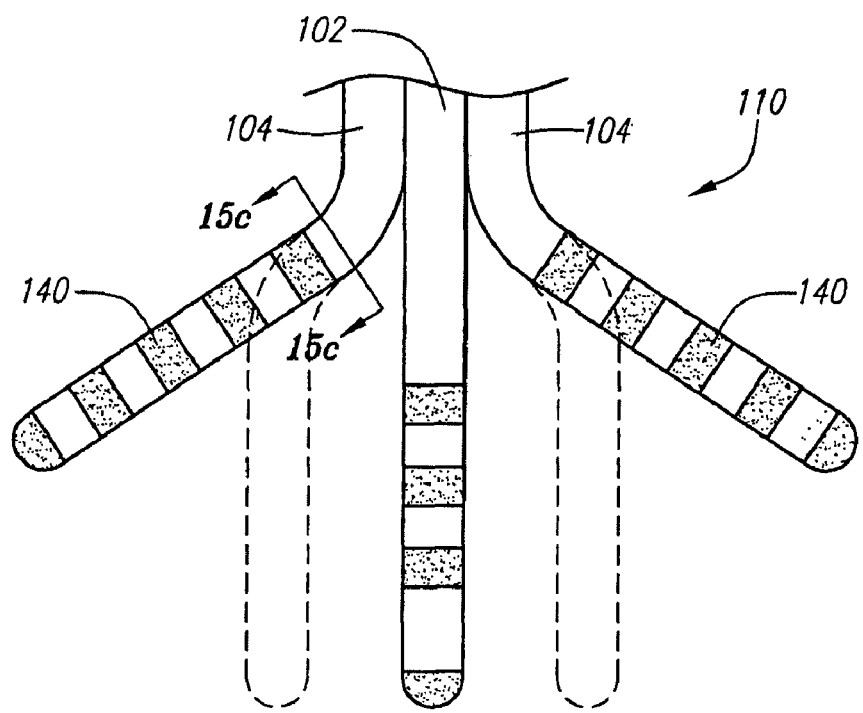
FIG. 14c is a cutaway top view of another alternative stimulation lead assembly that can be formed from the kit of FIG. 1 when the primary stimulation lead of FIG. 13 is used, wherein the secondary stimulation leads can be placed into a curved geometry that converges towards the primary stimulation lead when a pullwire is tensioned.
Figure 15C:
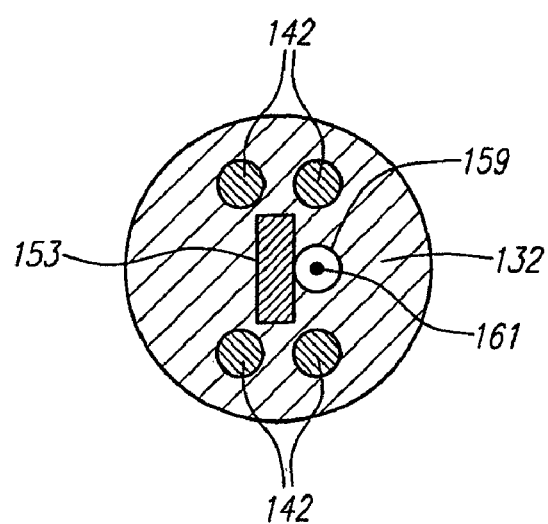
FIG. 15c is a cross-sectional view of the stimulation lead assembly of FIG. 14c, taken along the line 15c-15c.

As another alternative, a steering mechanism can be used to control the shape of the secondary stimulation lead 104. In particular, as illustrated in FIG. 14*c*, the distal ends of the secondary stimulation leads 104 normally exhibit a straight geometry, in which case, the resilient member 153 is likewise formed into a straight geometry. As illustrated in FIG. 15*c*, the secondary stimulation lead 104 comprises a pullwire lumen 159 and an associated pullwire 161 mounted to the inside surface of the distal end of the resilient member 153. When the pullwire 161 is relaxed, the distal end of the secondary stimulation lead 104 assumes the straight geometry. In this case, the distal ends of the secondary stimulation leads 104 diverge from the primary stimulation lead 102, as illustrated in FIG. 14*c*. In contrast, when the pullwire 161 is pulled, the distal end of the secondary stimulation lead 104 assumes a geometry (shown in phantom) that curves inward towards the primary stimulation lead 102. Notably, the proximal-most portion of the distal ends of the secondary stimulation leads 104 does not contain the resilient member 153, so that the respective stimulation lead 104 bends at this portion when the pullwire 161 is pulled. Rather than providing a normally straight secondary stimulation lead 104, the distal end of the secondary stimulation lead 104 can be pre-curved much like the stimulation lead 104 illustrated in FIG. 14*a*. In this case, the pullwire 161 can be mounted to the outside surface of the distal end of the resilient member 153, such that relaxation of the pullwire 161 causes the distal end of the secondary stimulation lead 104 to assume a curved geometry that converges towards the primary stimulation lead 102, whereas the application of tension on the pullwire 161 causes the distal end of the secondary stimulation lead 104 to assume a lesser curved or straight geometry that diverges from the primary stimulation lead 102.

Figure 14D:
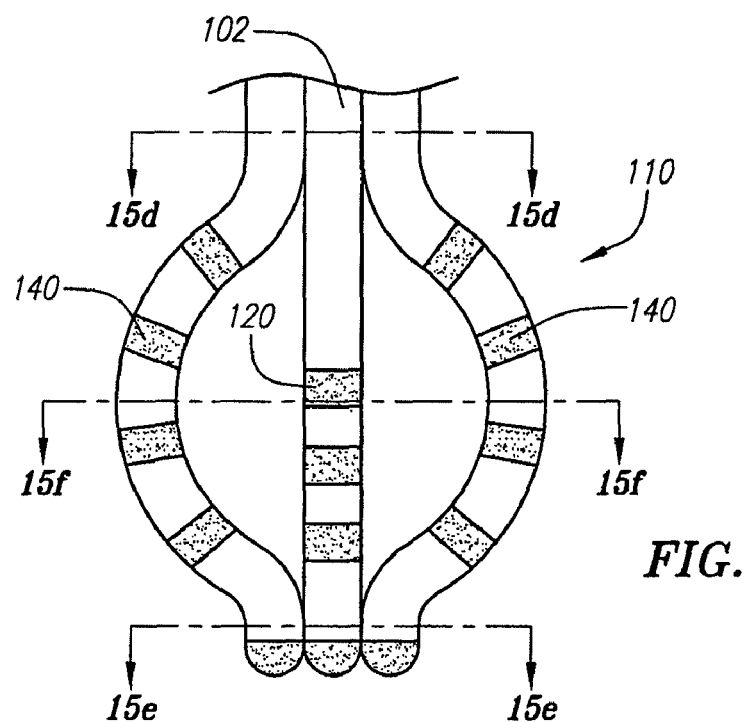
FIG. 14d is a cutaway top view of still another alternative stimulation lead assembly that can be formed from the kit of FIG. 1 when the primary stimulation lead of FIG. 3 is used, wherein the secondary stimulation leads can be placed into a curved geometry that bows away from the primary stimulation lead.
Figure 15D:
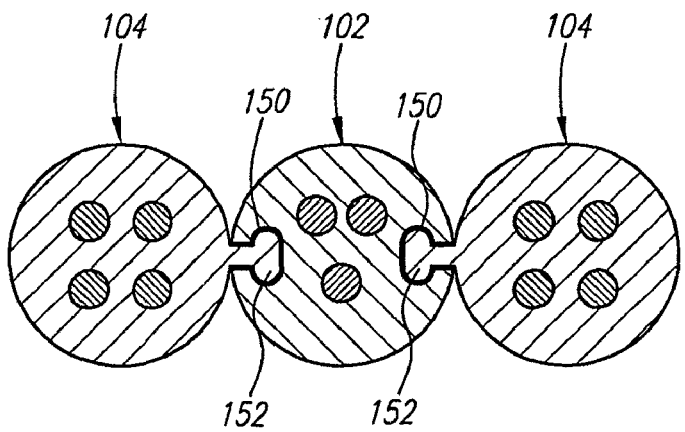
FIG. 15d is a cross-sectional view of the stimulation lead assembly of FIG. 14d, taken along the line 15d-15d.
Figure 15E:
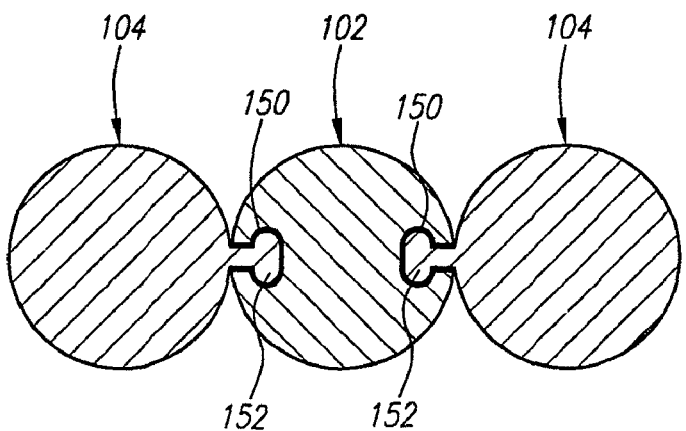
FIG. 15e is a cross-sectional view of the stimulation lead assembly of FIG. 14d, taken along the line 15e-15e.
Figure 15F:
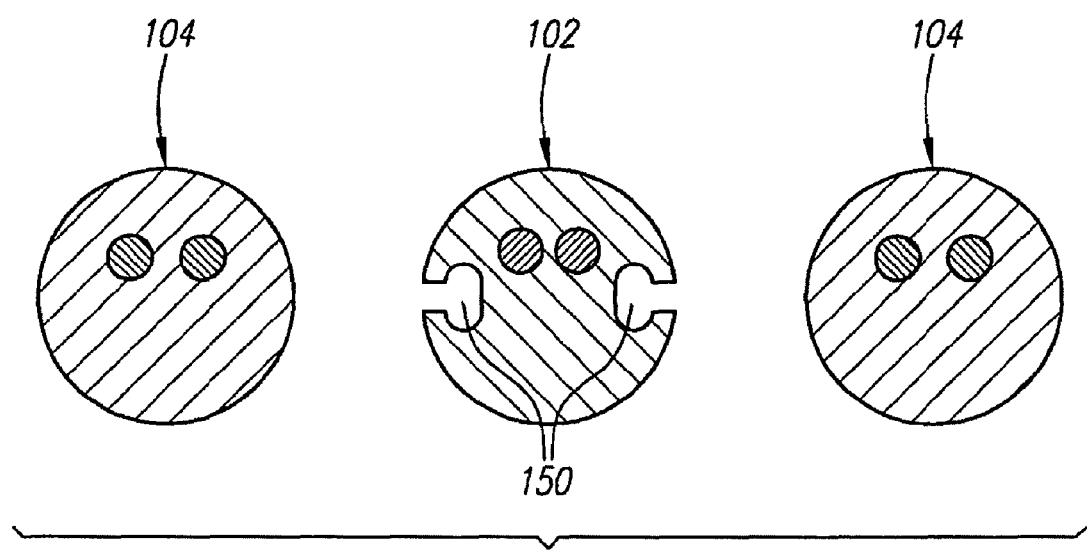
FIG. 15f is a cross-sectional view of the stimulation lead assembly of FIG. 14d, taken along the line 15f-15f.

As still another alternative, a portion of the secondary stimulation lead 104 may not have a rail, so that it bows outward after the primary stimulation lead 102 and secondary stimulation lead 104 are fully engaged, as illustrated in FIG. 14*d*. As best seen in FIGS. 15*d-f*, the rail 152 extends along the distal-most and proximal-most portions of the distal end of the second stimulation lead 104, but does not extend along a medial-portion of the distal end of the second stimulation lead 104. As a result, after the distal end of the respective rail 152 (i.e., the rail 152 located on the distal-most portion of the second stimulation lead 104) abuts the distal rail stop (not shown) in the corresponding slot 150, further distal movement of the secondary stimulation lead 104 relative to the primary stimulation lead 102 causes the medial-portion, which is not engaged with the slot 150 of the primary stimulation lead 102, to bow outward from a straight geometry (shown in phantom). In contrast, proximal movement of the secondary stimulation lead 104 relative to the primary stimulation lead 102 causes the medial-portion to return from the bowed geometry back to its straight geometry.

Figure 6:
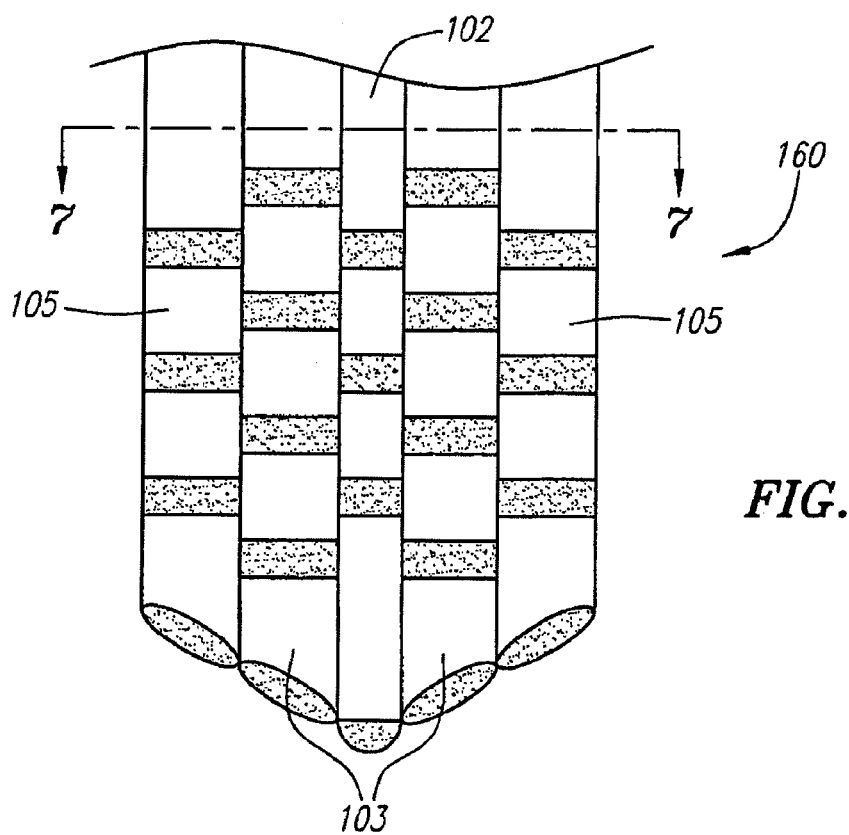
FIG. 6 is a cutaway view of an alternative stimulation lead assembly that can be formed from the kit of FIG. 1.
Figure 7:
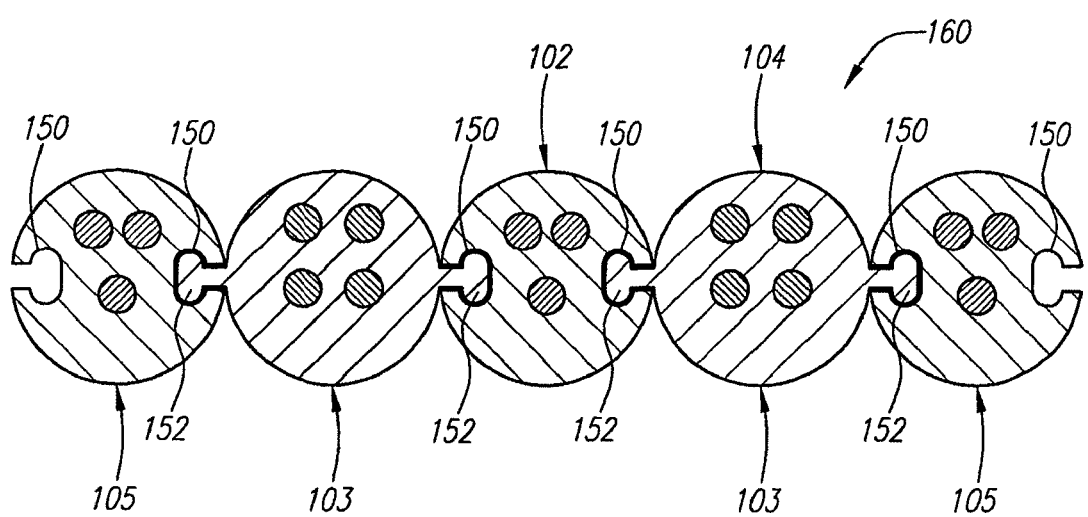
FIG. 7 is a cross-sectional view of the stimulation lead assembly of FIG. 6, taken along the line 7-7.

It should be noted that although the assemblies 110 illustrated in FIGS. 2 and 14*a-d* are formed of three stimulation leads, less or more than three stimulation leads can be used. For example, if an assembly formed only of two stimulation leads is desired, only one slot 150 on the primary stimulation lead 102 is required. In this case, the primary stimulation lead 102 may only have one slot 150 formed along one side of the respective body 112, or alternatively, if the primary stimulation lead 102 comprises two opposing slots 150, only one will be used to couple the lone secondary stimulation lead 104 thereto. On the other hand, if an assembly formed of more than three stimulation leads is desired, the secondary stimulation leads 104 may have a pair of circumferentially opposed rails 152. For example, if there are five stimulation leads, two secondary stimulation leads 103 (which are similar to the secondary stimulation leads 104, but with a pair of circumferentially opposing rails 152) can be coupled to the primary stimulation lead 102 by sliding the rails 152 of the respective secondary stimulation leads 104 along the respective slots 150 of the primary stimulation lead 102, thereby forming a partial assembly similar to that illustrated in FIG. 3. Then, two additional secondary stimulation leads 105 (which are similar to secondary stimulation leads 105, but have a pair of circumferentially opposed slots 150) can be coupled to the secondary stimulation leads 105 by sliding the slots 150 of the additional secondary stimulation leads 102 along the respective rails 152, thereby forming a full assembly 160, as illustrated in FIGS. 6 and 7.

Referring back to FIG. 1, the implantable stimulation source 106 is designed to deliver electrical pulses to the stimulation leads 102/104 in accordance with programmed parameters. In the preferred embodiment, the stimulation source 106 is programmed to output electrical pulses having amplitudes varying from 0.1 to 20 volts, pulse widths varying from 0.02 to 1.5 milliseconds, and repetition rates varying from 2 to 2500 Hertz. In the illustrated embodiment, the stimulation source 106 takes the form of a totally self-contained generator, which once implanted, may be activated and controlled by an outside telemetry source, e.g., a small magnet. In this case, the pulse generator has an internal power source that limits the life of the pulse generator to a few years, and after the power source is expended, the pulse generator must be replaced. Generally, these types of stimulation sources 106 may be implanted within the chest or abdominal region beneath the skin of the patient.

Alternatively, the implantable stimulation source 106 may take the form of a passive receiver that receives radio frequency (RF) signals from an external transmitter worn by the patient. In this scenario, the life of the stimulation source 106 is virtually unlimited, since the stimulation signals originate from the external transmitter. Like the self-contained generators, the receivers of these types of stimulation sources 106 can be implanted within the chest or abdominal region beneath the skin of the patient. The receivers may also be suitable for implantation behind the ear of the patient, in which case, the external transmitter may be worn on the ear of the patient in a manner similar to that of a hearing aid. Stimulation sources, such as those just described, are commercially available from Advanced Neuromodulation Systems, Inc., located in Plano, Tex., and Medtronic, Inc., located in Minneapolis, Minn.

The optional extension lead 108 comprises an elongated sheath body 144 having a proximal end 146 and a distal end 148, much like the sheath bodies 112/132 of the stimulation leads 102/104, a distal adapter 154 coupled to the distal end 148 of the sheath body 144, a connector 156 coupled to the proximal end 146 of the sheath body 144, and a plurality of electrical conductors (not shown) extending through the sheath body 144. The length of the extension lead 108 is sufficient to extend from the spine of the patient, where the proximal ends of the implanted stimulation leads 102/104 protrude from to the implantation site of the stimulation source 106—typically somewhere in the chest or abdominal region. The distal adapter 154 is configured to receive the proximal ends of the stimulation leads 102/104, and the proximal connector 156 is configured to couple to the stimulation source 106.

Figure 8A:
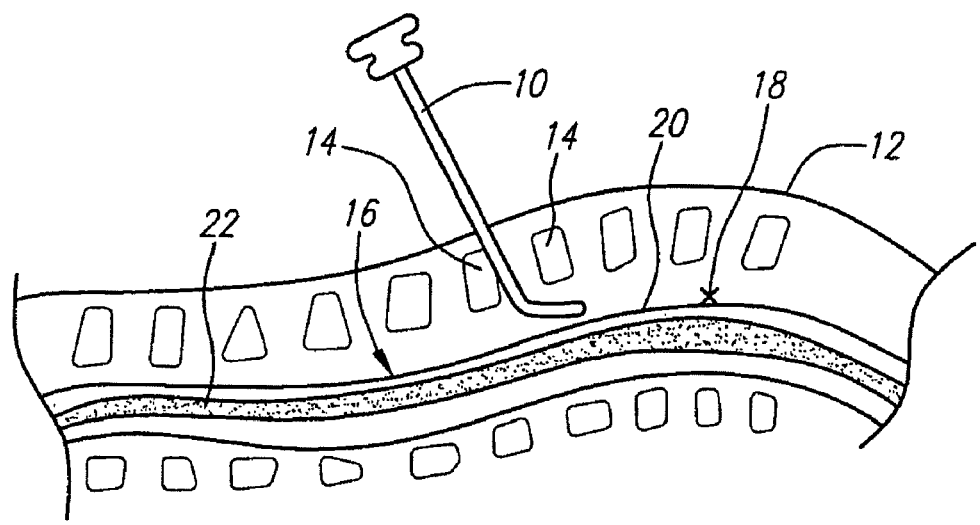
FIGS. 8A-8D are various views illustrating the installation of the kit of FIG. 1 into a patient's spine.

Having described the stimulation lead kit 100, its installation and use in treating chronic pain will now be described with reference to FIGS. 8A-8D. After the patient has been prepared (which may involve testing the efficacy of spinal cord stimulation on the patient, and, once determining that the patient can be effectively treated with spinal cord stimulation, identifying and marking the appropriate vertebral intervals on the patient's skin and applying a local anesthetic to this region), a needle 10, such as, e.g., a Touhy needle, is inserted through the patient's skin 12 between the desired vertebrae 14, and into the epidural space 16 within the spine at a position inferior to target stimulation site 18 (FIG. 8A). In the illustrated method, the Touhy needle 10 will serve as the primary delivery mechanism for the primary stimulation lead 102. Alternatively, if an optional introducer (not shown) is used, a guide wire (not shown) is introduced through the needle 10 and advanced to or near the target stimulation site 18. The needle 10 is removed, the introducer is then introduced over the guide wire and advanced to the target stimulation site 18, and the guide wire is then withdrawn. In this case, the introducer will serve as the primary delivery mechanism for the primary stimulation lead 102.

Figure 8B:
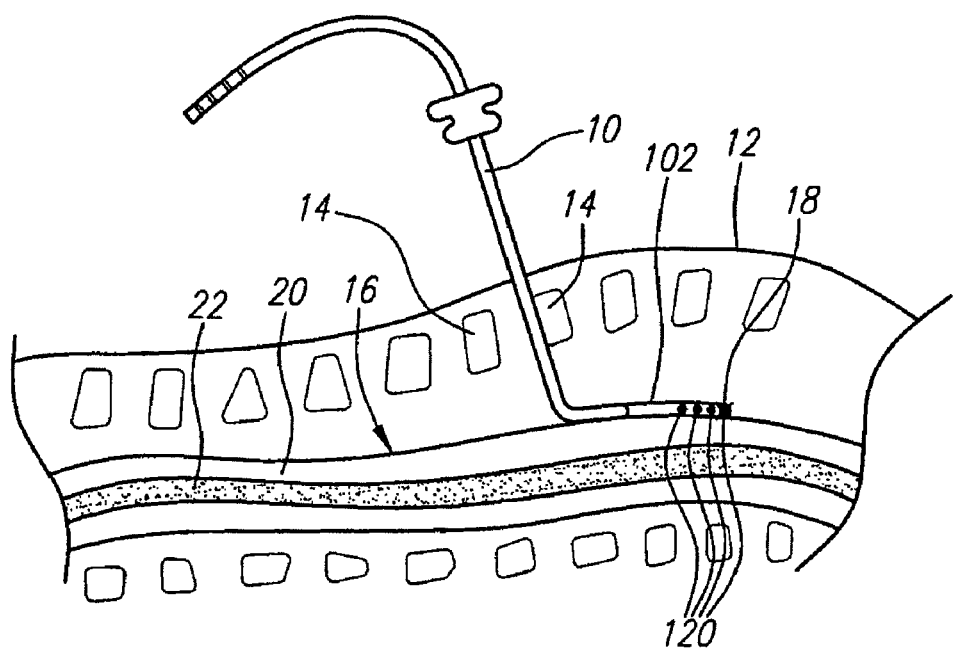
Figure 8C:
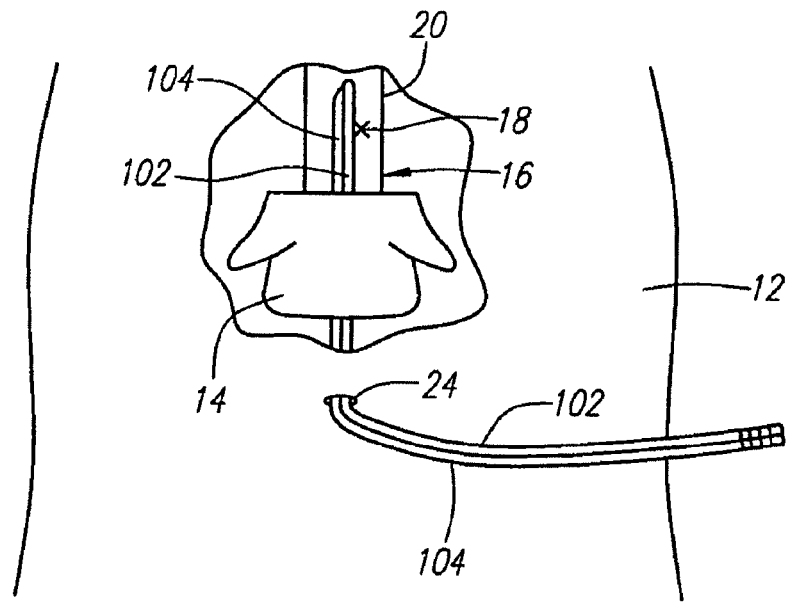
Figure 8D:
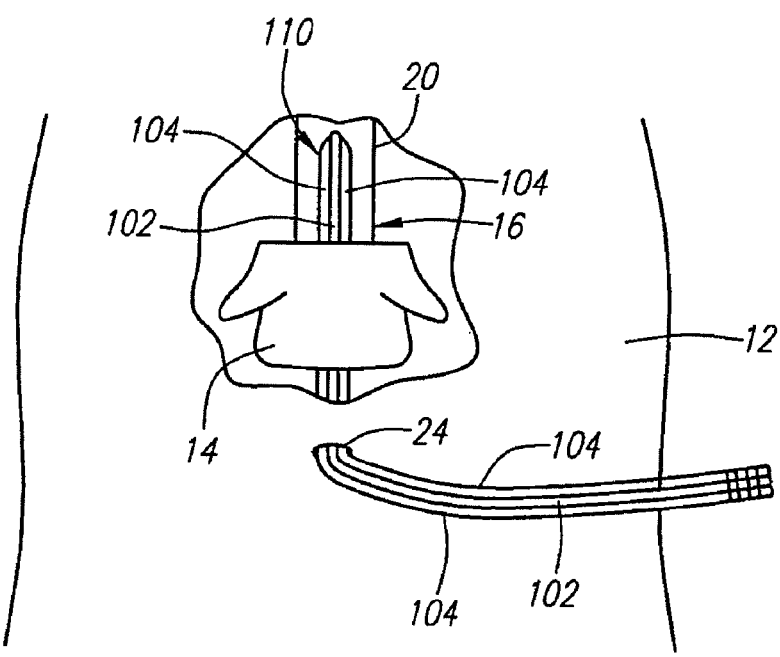

After the deliver mechanism is in place, the primary stimulation lead 102 is then inserted through the needle or the introducer (whichever is in place), and positioned in the epidural space at the target stimulation site 18, with the electrodes 120 facing the dural layer 20 surrounding the spinal cord 22 (FIG. 8B). If the primary stimulation lead 102 has a stylet lumen, a stylet can be used to provide additional axial stiffness and to facilitate control. Next, the needle 10 or introducer is removed, and one of the secondary stimulation leads 104 is delivered through the percutaneous opening 24 left by the removal of the needle 10, and into the epidural space 16 by slidably engaging the secondary stimulation lead 104 along the primary stimulation lead 102 (FIG. 8C). In particular, the rail 152 of the secondary stimulation lead 104 is inserted into the corresponding slot 150 of the primary stimulation lead 102, and the secondary stimulation lead 104 is pushed until the distal end of the rail 152 abuts the distal end of the slot 150, thereby signifying that the secondary stimulation lead 104 is fully engaged with the primary stimulation lead 102 (with the electrodes 120/140 of the stimulation leads 102/104 adjacent, but offset from, each other) and is in its proper location within the epidural space 16 of the patient. The other secondary stimulation lead 104 is then delivered into the epidural space by slidably engaging it along the primary stimulation lead 102 in the same manner, thereby completing the stimulation lead assembly 110 (FIG. 8D). If the secondary stimulation leads 104 have stylet lumens, a stylet can be used to provide additional axial stiffness and to facilitate control. Once the assembly 110 is completed, the electrodes 120/140 will span the midline of the spinal cord 22, much like the electrodes of a standard surgical lead do.

Next, the proximal ends of the stimulation leads 102/104 are connected to a tester (not shown), which is then operated in a standard manner to confirm proper location of the stimulation lead assembly 110 and to adjust the stimulation parameters for optimal pain relief. Once this optimization process has been completed, the tester is disconnected from the stimulation leads 102/104, which are then anchored in place using standard lead anchors (not shown). Next, the stimulation lead assembly 110 is coupled to the stimulation source 106 and implantation is completed (not shown). In particular, a subcutaneous pocket is created in the patient's abdominal area for implantation of the stimulation source 106, and a tunnel is subcutaneously formed between the spine region and the subcutaneous pocket. The optional lead extension 108 is passed through the tunnel, after which the adapter 154 of the extension 108 is connected to the proximal ends of the stimulation leads 102/104 and the connector 156 of the lead extension 108 is connected to the stimulation source 106. The stimulation source 106 is programmed and tested, and then placed within the subcutaneous pocket, after which all incisions are closed to effect implantation of the stimulation lead assembly 110 and stimulation source 106. The stimulation source 106 can then be operated to convey stimulation energy from the stimulation source 106 to the electrodes 120/140 of the stimulation lead assembly 110, where it is, in turn, conveyed into the neural tissue for pain relief. If necessary or desired, e.g., if the electrodes 120/140 malfunction or stimulation otherwise ceases to provide therapeutic benefit, the stimulation lead assembly 110 can be subsequently retrieved from the patient's spine by removing the assembly 110 at the same time or by removing the assembly one stimulation lead 102/104 at a time by slidably disengaging the stimulation leads 102/104. In the case of the assembly 110 illustrated in FIG. 14, the rail and slot arrangement will pull the deployed distal end of the secondary stimulation leads 104 along side of the primary stimulation lead 102 when retrieved.

It can be appreciated that the relatively large footprint made by the stimulation lead assembly 110, much like a prior art surgical lead, provides a more stable platform for the electrodes 120/140. Also, like a prior art surgical lead, the electrodes 120/140 face in a single direction, thereby focusing the stimulation energy into the affected neural tissue where it is needed. Unlike a surgical lead, however, the stimulation lead assembly 110 can be percutaneously delivered into the patient's spine in a minimally invasive and relatively pain-free manner, without requiring extensive patient recovery.

Figure 9:
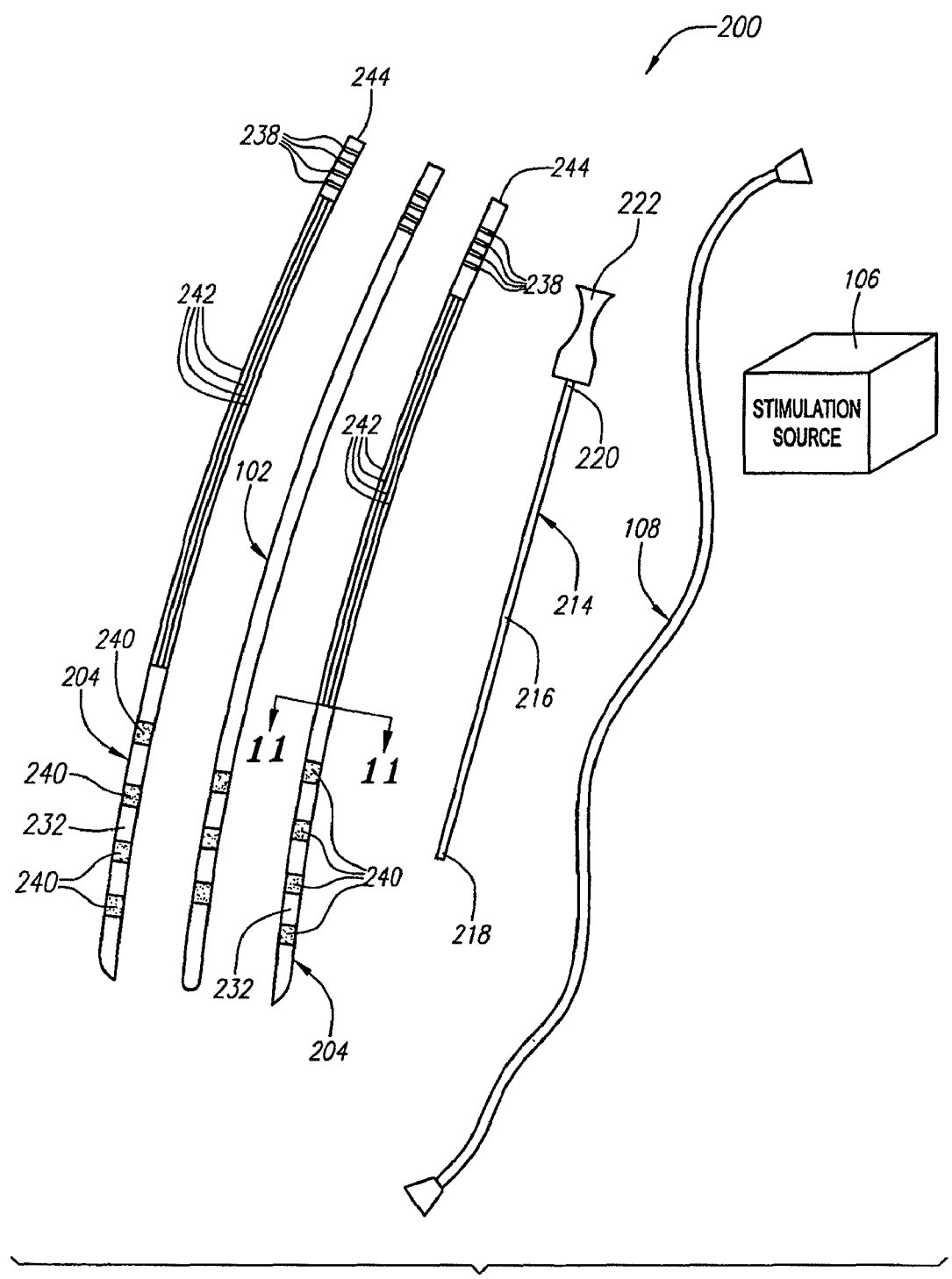
FIG. 9 is a plan view of another modular stimulation lead kit arranged in accordance with another preferred embodiment of the present invention.

Referring now to FIG. 9, a modular stimulation lead kit 200 arranged in accordance with another preferred embodiment of the present invention is shown. The kit 200 is similar to the previously described kit 100, with the exception that the kit 200 comprises secondary stimulation leads 204 that minimize the profile of the resulting assembly (shown in FIG. 10), as it exits the spine of the patient. In particular, each secondary stimulation lead 204 comprises a shortened sheath body 232, electrodes 240 mounted to the sheath body 232, electrical conductors 242 extending from the sheath body 232, and a connector 244 that receives the proximal ends of the electrical conductors 242. The connector 244 comprises a plurality of terminals 238 that are similar to the previously described lead terminals 138. The sheath body 232 is composed of the same material and has the same general shape as the sheath body 132 of the previously described secondary stimulation lead 104. The sheath body 232, as illustrated in FIG. 9, however, is much shorter, so that it can be entirely received within the epidural space of the patient, i.e., the sheath body 232 will not extend out of the patient's back when fully deployed within the epidural space. The electrical conductors 242, because they are exposed, are preferably composed of an electrically insulative material.

Figure 11:
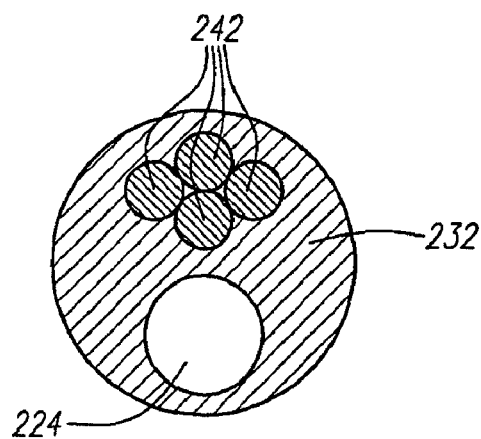
FIG. 11 is a cross-sectional view of the secondary stimulation lead of FIG. 10, taken along the line 11-11.

The kit 200 further comprises a pusher 214 that can be used to facilitate introduction of the respective secondary stimulation lead 204 along the primary stimulation lead 102 once the entire sheath body 232 of the secondary stimulation lead 204 is within the patient's back. The pusher 214 comprises a cylindrical rod 216 having a distal tip 218 and a proximal end 220, and a handle 222 mounted on the proximal end 220 of the rod 216. The distal tip 218 of the rod 216 is adapted to be received within an opening 224 (shown in FIG. 11) at the proximal end of the sheath body 232, thereby facilitating stable engagement between the pusher 214 and respective secondary stimulation lead 204.

Figure 12A:
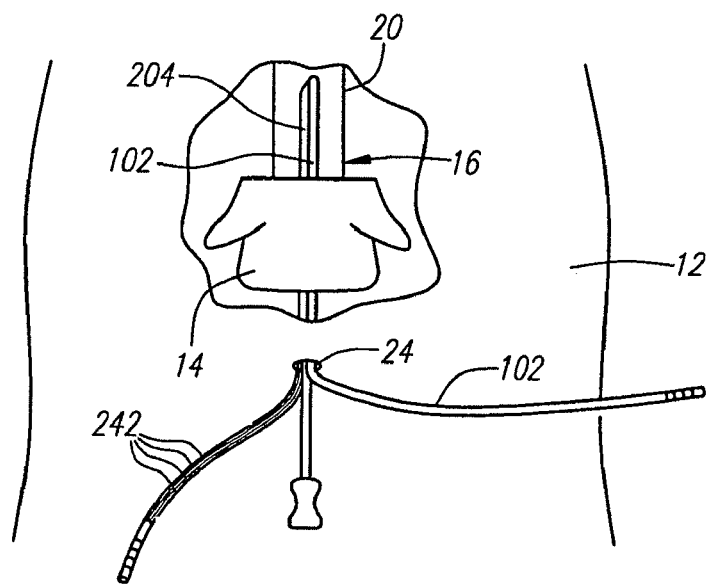
FIGS. 12A-12B are various views illustrating the installation of the kit of FIG. 9 into a patient's spine.
Figure 12B:
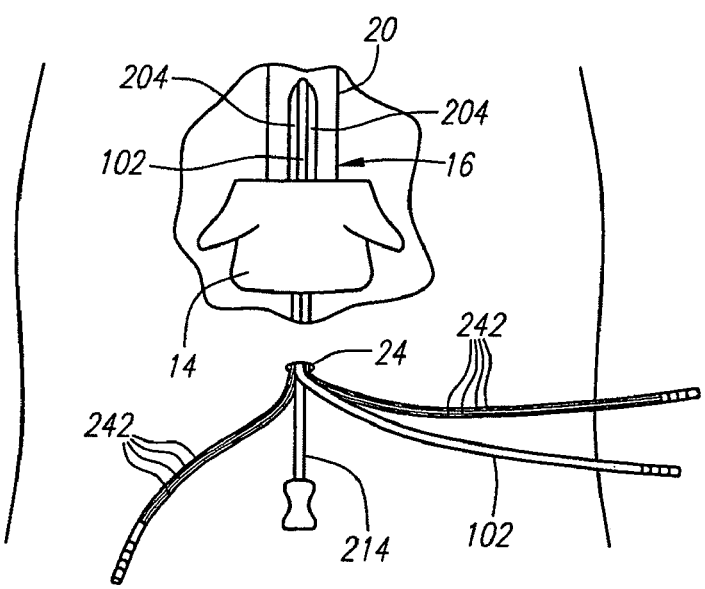

The kit 200 can be installed and used in the same manner as the previously described kit 100 in treating chronic pain. In particular, the patient is prepared and the primary stimulation lead 102 is delivered into the epidural space 16 of the patient's spine, so that the electrodes 120 are placed adjacent the target stimulation site 18 in the same manner described above with respect to FIGS. 8A and 8B. One of the secondary stimulation leads 204 is then delivered into the epidural space 16 in the same manner as the secondary stimulation lead 104 described above was delivered, with the exception that the pusher 214 is used to advance the secondary stimulation lead 204 along the primary stimulation lead 102 until fully deployed within the epidural space 16 (FIG. 12A). The remaining stimulation lead 204 is delivered into the epidural space 16 in the same manner to complete the stimulation lead assembly 210 (FIG. 12B).

Notably, because the percutaneous opening 24 need only support, at most, two sheath bodies at one time, it can be made smaller, or alternatively, additional stimulation leads with shortened sheath bodies can be introduced within the epidural space 16 without increasing the size of the percutaneous opening. After the stimulation lead assembly 210 has been formed within the epidural space, it is tested and optimized. The extension lead 108 is then connected between the stimulation leads 102/204 and the stimulation source 106, and the incisions are closed to fully implant the system, as previously described above.

Figure 16:
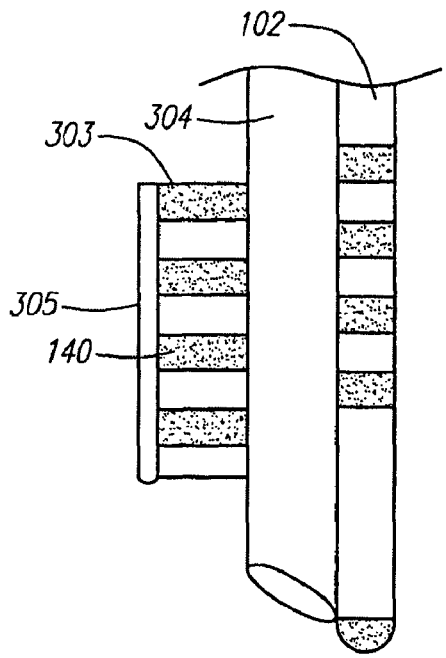
FIG. 16 is a cutaway top view of an alternative stimulation lead assembly.

Referring now to FIG. 16, an alternative embodiment of a secondary stimulation lead 304 engaged with one side of the primary stimulation 102 is illustrated. Although not shown, another secondary stimulation lead 304 can be engaged with the opposite side of the primary stimulation lead 102. The secondary stimulation lead 304 is similar to the previously described secondary stimulation lead 104, with the exception that the secondary stimulation lead 304 comprises a flap 303 on which the electrodes 140 are mounted. The secondary stimulation lead 304 can, alternatively, have a shortened sheath body much like the secondary stimulation lead 204 illustrated in FIG. 9. The flap 303 is designed to be constrained by the primary stimulation lead 102 to facilitate percutaneous delivery of the secondary stimulation lead 102, and released by the primary stimulation lead 102 to deploy the electrodes 140 into contact with the neural tissue.

Figure 17:
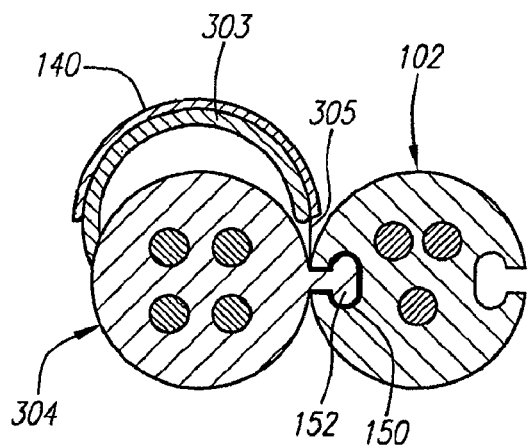
FIG. 17 is a cross-sectional view of a portion of the stimulation lead assembly of FIG. 16, particularly showing an electrode flap of a secondary stimulation lead constrained by the primary stimulation lead.
Figure 18:
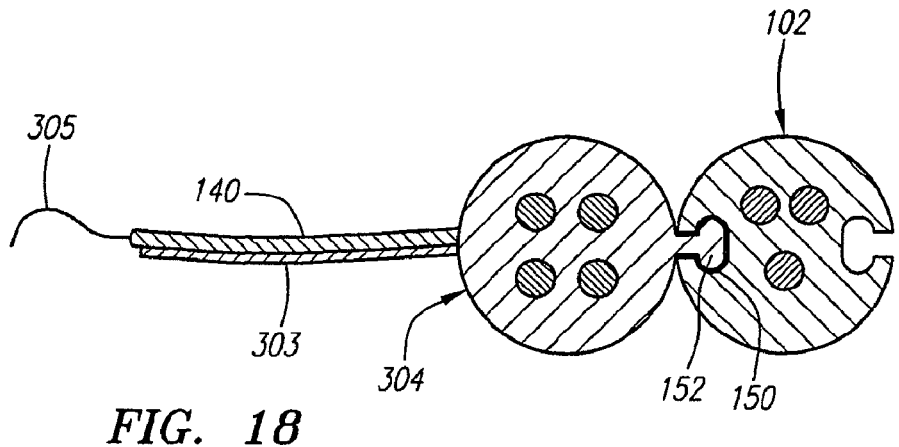
FIG. 18 is a cross-sectional view of a portion of the stimulation lead assembly of FIG. 16, particularly showing the electrode flap of the secondary stimulation lead released by the primary stimulation lead.

In particular, the edge of the flap 303 comprises a coupling mechanism 305 that is designed to fit snugly within the respective slot 150 of the primary stimulation lead 102, along with the rail 152 of the secondary stimulation lead 102, when the secondary stimulation lead 304 is slidably engaged with the primary stimulation lead 102, as illustrated in FIG. 17. As the rail 152 of the secondary stimulation lead 102 exits the slot 150 of the primary stimulation lead 102, however, the coupling mechanism 305 of the flap 303 will release from the slot 150, thereby allowing the flap 303 to deploy, placing the electrodes 140 into contact with the underlying tissue, as illustrated in FIG. 18. It should be noted, that, when the secondary stimulation lead 304 is used in the kit 100 or kit 200, the slots 150 in the primary stimulation lead 102 will not terminate as hereinbefore described, but will rather open up at the distal tip of the primary stimulation lead 102, so that the flap 303 can exit the respective slot 150 and be released by the primary stimulation lead 102.

Figure 10:
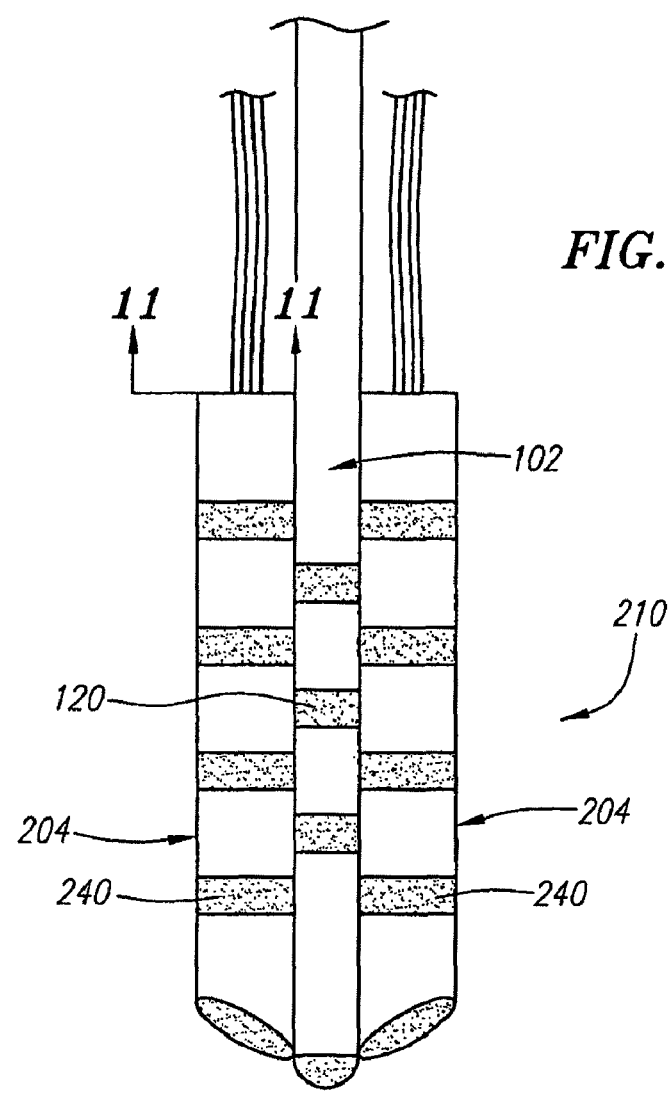
FIG. 10 is a cutaway top view of a stimulation lead assembly formed from the kit of FIG. 9.

Installation and use of the secondary stimulation lead 304 in forming the stimulation lead assembly 110 illustrated in FIG. 2, or alternatively the stimulation lead assembly 210 illustrated in FIG. 10, is similar that previously described above.

Although in all of the previous embodiments, the primary stimulation lead 102 was used to provide a means of guiding the secondary stimulation leads 104 into the percutaneous opening within the patient and adjacent the target tissue region, as well as to provide a means of stimulating the tissue region, a guide member similar to the primary stimulation lead 102, but lacking stimulation capability, can be alternatively used to similarly guide the secondary stimulation leads 104 through the percutaneous opening to the target tissue region. In this case, only the secondary stimulation leads 104 will be used to stimulate tissue.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical kit, comprising:
a first medical lead comprising a first elongated body, a first operative element, and a first coupling mechanism longitudinally extending along at least a portion of the first elongated body; and
a second medical lead comprising a second elongated body, a second operative element, and a first complementary coupling mechanism configured to slidably engage the first coupling mechanism, wherein the second elongated body is configured for being deployed from the first elongated body by slidably disengaging at least a portion of the complementary coupling mechanism from the coupling mechanism.

2. The medical kit of claim 1, wherein at least one of the first and second elongated bodies is cylindrically-shaped.

3. The medical kit of claim 1, wherein the greatest cross-sectional dimension of at least one of the first and second elongated bodies is 5 mm or less.

4. The medical kit of claim 1, wherein the first and second operative elements are electrodes.

5. The medical kit of claim 1, wherein the first and second operative elements are mounted on the respective first and second elongated bodies.

6. The medical kit of claim 1, wherein the first and second operative elements are configured to face a single direction when the first complementary coupling mechanism slidably engages the first coupling mechanism.

7. The medical kit of claim 1, wherein each of the first and second medical leads comprises a plurality of operative elements.

8. The medical kit of claim 1, wherein the first coupling mechanism and first complementary coupling mechanism are configured to slidably engage each other in a rail and slot arrangement.

9. The medical kit of claim 1, wherein the second complementary coupling mechanism extends along only a distal portion of the second elongated body.

10. The medical kit of claim 1, wherein the second elongated body is shorter than the first elongated body.

11. The medical kit of claim 1, wherein the second elongated body is configured for being actively changed from a first geometry to a second geometry after deployment from the first elongated body.

12. The medical kit of claim 1, wherein the second elongated body is pre-curved.

13. The medical kit of claim 1, wherein the first medical lead comprises another coupling mechanism longitudinally extending along at least a portion of the first elongated body, the medical kit further comprising a third medical lead comprising a third elongated body, an operative element mounted on the third elongated body, and another complementary coupling mechanism configured to slidably engage the other coupling mechanism.

14. The medical kit of claim 1, wherein the second elongated body is shorter than the first elongated body, such that a proximal end of the first elongated body is configured for extending from an opening in the patient's back to a location external to the patient when a distal end of the first elongated body is disposed within the patient's spine, and the second elongated body is configured for being entirely received within the patient's spine when the complementary coupling mechanism is slidably engaged with the coupling mechanism when the proximal end of the first elongated body extends from the opening in the patient's back.

15. A method of treating a disorder in a patient using the medical kit of claim 1, comprising:
delivering the first medical lead into the patient;
delivering the second medical lead into the patient by sliding the complementary coupling mechanism along the coupling mechanism.

16. The method of claim 15, wherein the first and second medical leads are delivered into the patient through a percutaneous opening.

17. A medical kit, comprising:
a first medical lead comprising a first elongated body, a first operative element, and a first coupling mechanism longitudinally extending along at least a portion of the first elongated body; and
a second medical lead comprising a second elongated body, a second operative element, and a first complementary coupling mechanism configured to slidably engage the first coupling mechanism, wherein the second elongated body is configured to be actively changed from a first geometry to a second geometry after deployment from the first elongated body.

18. The medical kit of claim 17, further comprising a stylet configured to be introduced through the second elongated body to change the second elongated body from the first geometry to the second geometry.

19. The medical kit of claim 17, wherein the second medical lead comprises a pullwire configured to be pulled to change the second elongated body from the first geometry to the second geometry.

20. A medical kit, comprising:
a first medical lead comprising a first elongated body, a first operative element, and a first coupling mechanism longitudinally extending along at least a portion of the first elongated body; and
a second medical lead comprising a second elongated body, a second operative element, and a first complementary coupling mechanism configured to slidably engage the first coupling mechanism, wherein the complementary coupling mechanism does not extend along a portion of the second elongated body, and the second elongated body is configured to deploy from the first elongated body by bowing the portion of the second elongated body away from the first elongated body.

21. A medical kit, comprising:
a first medical lead comprising a first elongated body, a first operative element, and a first coupling mechanism longitudinally extending along at least a portion of the first elongated body; and
a second medical lead comprising a second elongated body, a second operative element, and a first complementary coupling mechanism configured to slidably engage the first coupling mechanism, wherein the second medical lead comprises a flap on which the respective operative element is disposed, the flap extending along a portion of the complementary coupling mechanism, and configured to be secured by the coupling mechanism when the portion of the complementary coupling mechanism slidably engages the coupling mechanism and released by the coupling mechanism when the portion of the complementary coupling mechanism slidably disengages the coupling mechanism.

22. A method of performing a medical procedure on a patient, comprising:
  delivering a first medical lead into the patient;
  delivering a second medical lead into the patient by slidably engaging the second medical lead along the first medical lead; and
  deploying the second medical lead from the first medical lead.

23. The method of claim 22, wherein the first and second medical leads are delivered into the patient through a percutaneous opening.

24. The method of claim 22, further comprising implanting the first and second medical leads within the patient.

25. The method of claim 22, further comprising delivering a third medical lead into the patient by slidably engaging the third medical lead along the first medical lead.

26. The method of claim 22, further comprising inserting a delivery device into the patient, wherein the first medical lead is introduced through the delivery device into the patient.

27. The method of claim 26, wherein the delivery device is one of an introducer or needle.

\* \* \* \* \*